(12) United States Patent
Van Benthem et al.

(10) Patent No.: US 8,266,197 B1
(45) Date of Patent: *Sep. 11, 2012

(54) METHOD FOR FACTOR ANALYSIS OF GC/MS DATA

(75) Inventors: Mark H. Van Benthem, Albuquerque, NM (US); Paul G. Kotula, Albuquerque, NM (US); Michael R. Keenan, Wolcott, NY (US)

(73) Assignee: Sandia Corporation, Albuquerque, NM (US)

( * ) Notice: Subject to any disclaimer, the term of this patent is extended or adjusted under 35 U.S.C. 154(b) by 292 days.

This patent is subject to a terminal disclaimer.

(21) Appl. No.: 12/754,041

(22) Filed: Apr. 5, 2010

Related U.S. Application Data

(63) Continuation-in-part of application No. 11/233,223, filed on Sep. 22, 2005, now Pat. No. 7,725,517.

(60) Provisional application No. 60/614,867, filed on Sep. 29, 2004.

(51) Int. Cl.
G06F 7/38 (2006.01)
G01N 31/10 (2006.01)

(52) U.S. Cl. .......................... 708/446; 702/23

(58) Field of Classification Search .................. 708/446, 708/520; 702/22, 23
See application file for complete search history.

(56) References Cited

U.S. PATENT DOCUMENTS

| | | | | |
|---|---|---|---|---|
| 6,377,907 | B1 * | 4/2002 | Waclawski | 702/182 |
| 6,584,413 | B1 * | 6/2003 | Keenan et al. | 702/28 |
| 7,127,095 | B2 | 10/2006 | El Fakhri et al. | 382/128 |
| 7,283,684 | B1 * | 10/2007 | Keenan | 382/276 |
| 7,451,173 | B1 * | 11/2008 | Van Benthem et al. | 708/607 |
| 2007/0005391 | A1 * | 1/2007 | Repucci et al. | 705/1 |

OTHER PUBLICATIONS

I. S. Begley, "Characterisation and Correction of Instrumental Bias in Inductively Coupled . . . ," Journal of Analytical Atomic Spectrometry, Apr. 1997, 395-402, vol. 12.
R. Bro, "A Fast Non-Negativity-Constrained Least Squares Algorithm," Journal of Chemometrics, vol. 11, 393-401 (1997).
B. E. Abbassi, "Automataic Extraction of Relevant Peaks and Reconstruction of . . . ," International Journal of Mass Spectrometry and Ion Processes, 141, (1995) 171-186.
P. Geladi, "Partial Least-Squares Regression: A Tutorial," Analytica Chimica Acta, 185 (1986) 1-17, Elsevier.
C. Hackett, "Laser Ablation Sampling for Induction Coupled Plasma Source Quadrupole Mass Spectrometry of Cd-Zn-Te . . . ," Journal of Electronic Materials, vol. 28, No. 6, 1999.
M. R. Keenan, "Optimal scaling of TOF-SIMS spectrum-images prior to multivariate statistical analysis," Applied Surface Science 231-232 (2004) 240-244, Elsevier.
M. R. Keenan, "Maximum likelihood principal component analysis of time-of-flight secondary ion mass . . . ," J. Vac. Sci. Technol. A, vol. 23, No. 4, Jul./Aug. 2005, 746-750.
M. R. Keenan, "Accounting for Poisson noise in the multivariate analysis of ToF-SIMS spectrum images\," Surface and Interface Analysis 2004; 36: 203-212.
M. R. Keenan, "Algorithms for Constrained Linear Unmixing with . . . ," Imaging Spectrometry VIII, Sylvia S. Shen, Editor, Proceedings of SPIE vol. 4816, 193-202 (2002).

(Continued)

*Primary Examiner* — Chuong D Ngo
(74) *Attorney, Agent, or Firm* — Kevin W. Bieg

(57) ABSTRACT

The method of the present invention provides a fast, robust, and automated multivariate statistical analysis of gas chromatography/mass spectroscopy (GC/MS) data sets. The method can involve systematic elimination of undesired, saturated peak masses to yield data that follow a linear, additive model. The cleaned data can then be subjected to a combination of PCA and orthogonal factor rotation followed by refinement with MCR-ALS to yield highly interpretable results.

13 Claims, 12 Drawing Sheets

OTHER PUBLICATIONS

P.G. Kotula, "Automated Analysis of SEM X-Ray Spectral Images: A Powerful New Microanalysis Tool," Microsc. Microanal. 9, 1-17, 2003.

R. Tauler, "Self-modelling curve resolution in studies of spectrometric titrations of multi-quilibria systems by factor analysis," Analytica Chimica Acta, 248 (1991) 447-458.

M. H. Van Benthem, "Application of equality constraints on variables during alternating least squares procedures," Journal of Chemometrics 2002, 16, 613-622.

M. H. Van Benthem, "Fast algorithm for the solution of large-scale non-negativity-constrained least squares problems," J. Chemometrics 2004, 18, 445-450.

* cited by examiner

METHOD FOR FACTOR ANALYSIS OF GC/MS DATA

CROSS-REFERENCE TO RELATED APPLICATIONS

This application is a continuation-in-part of application Ser. No. 11/233,223, filed Sep. 22, 2005, now U.S. Pat. No. 7,725,517, which claims the benefit of U.S. Provisional Application No. 60/614,867, filed Sep. 29, 2004, both of which are incorporated herein by reference.

STATEMENT OF GOVERNMENT INTEREST

This invention was made with Government support under contract no. DE-AC04-94AL85000 awarded by the U.S. Department of Energy to Sandia Corporation. The invention was made with the support of the U.S. Department of Homeland Security through interagency agreement no. HSHQDC-10-00041 with the U.S. Department of Energy. The Government has certain rights in the invention.

FIELD OF THE INVENTION

The present invention relates to spectral image analysis and, in particular, to a method for factor analysis of gas chromatography/mass spectroscopy (GC/MS) data.

BACKGROUND OF THE INVENTION

Several full-spectrum imaging techniques have been introduced in recent years that promise to provide rapid and comprehensive chemical characterization of complex samples. These spectroscopic imaging techniques include Electron Probe Microanalysis (EPMA), Scanning Electron Microscopy (SEM) with attached Energy Dispersive X-Ray Spectrometer (EDX), X-Ray Fluorescence (XRF), Electron Energy Loss spectroscopy (EELS), Particle Induced X-ray Emission (PIXE), Auger Electron Spectroscopy (AES), gamma-ray spectroscopy, Secondary Ion Mass Spectroscopy (SIMS), X-Ray Photoelectron Spectroscopy (XPS), Infrared Spectroscopy (IR), Raman Spectroscopy, Magnetic Resonance Imaging (MRI) scans, Computerized Axial Tomography (CAT) scans, IR reflectometry, Mass Spectrometry (MS), multidimensional chromatographic/spectroscopic techniques, hyperspectral remote imaging sensors, etc. These new spectroscopic imaging systems enable the collection of a complete spectrum at each point in a 1-, 2- or 3-dimensional spatial array. It is not uncommon that these spectral image data sets comprise tens of thousands of individual spectra, or more.

One of the remaining obstacles to adopting these techniques for routine use is the difficulty of reducing the vast quantities of raw spectral data to meaningful chemical information. Multivariate factor analysis techniques have proven effective for extracting the essential chemical information from high dimensional spectral image data sets into a limited number of components that describe the spectral characteristics and spatial distributions of the chemical species comprising the sample. In mathematical terms, given an m-pixel×n-channel matrix of spectral data D, we wish to approximate D by the matrix factorization $$D \approx CS^T \quad (1)$$

Here, C is an m-pixel×p-component matrix describing the distribution of the pure components at each spatial location and S is an n-channel×p-component matrix representation of the pure-component spectra. In the typical case that p<<m and n, the factorization in Eq. (1) accomplishes a large reduction in the dimensionality of the data set with the goal of optimally separating factors embodying real chemical information from those describing only noise.

It is well known, however, that factor-based methods suffer from a "rotational ambiguity." Given any invertible p×p transformation matrix R, D can be equally well expressed as $$D \approx CS^T = (CR)(R^{-1}S^T) = \underline{C}\,\underline{S}^T \quad (2)$$

That is, an infinite number of rotated factor pairs $\underline{C}$ and $\underline{S}$ will provide equally good fits to the data. The key to deriving relatively unique factors, then, is to select those factor solutions that satisfy additional optimization criteria. Thus, physically inspired constraints are often employed to derive relatively unique factor models that make the pure components more easily interpretable. In general, one would expect that the extent to which these criteria or constraints actually reflect the physical reality of a given sample, the higher the fidelity and reliability of the derived components.

Principal Component Analysis (PCA), used either by itself or to preprocess data, is the most ubiquitous tool of factor analysis. The constraints imposed by PCA are that the spectral and concentration factors must contain orthogonal components and that the components serially maximize the variance in the data that each accounts for. Neither constraint has any basis in physical reality; thus, the factors obtained via PCA are abstract and not easily interpreted. Alternating Least Squares-based Multivariate Curve Resolution (MCR-ALS) is another common factorization method used for spectral image analysis. This technique may force spectra and concentrations to be non-negative, for instance, yielding more physically realistic pure components. There are many cases, however, in which those constraints are not effective and where alternative approaches may provide new analytical insights.

For many cases of practical importance, imaged samples are "simple" in the sense that they consist of relatively discrete chemical phases. That is, at any given location, only one or a few of the chemical species comprising the entire sample have non-zero concentrations. In the limiting case that each location has only a single chemical component having non-zero concentration, the sample is said to be "perfectly simple." The methods of the present invention exploit this simplicity to make the resulting factor models more realistic. Therefore, more physically accurate and interpretable spectral and abundance components can be extracted from spectral images that have spatially simple structure.

In the present invention, the methods for spectral image analysis by exploiting spatial simplicity, as described in application Ser. No. 11/233,223, are adapted to provide a method for the fast, robust, and automated multivariate statistical analysis of gas chromatography/mass spectroscopy (GC/MS) data sets. The method can involve systematic elimination of undesired, saturated peak masses to yield data that follow a linear, additive model. The cleaned data can then be subjected to a combination of PCA and orthogonal factor rotation followed by MCR-ALS refinement to yield highly interpretable results.

SUMMARY OF THE INVENTION

The present invention is directed a method for factor analysis of GC/MS data, comprising measuring a mass-charge (m/z) spectrum of a sample with a gas chromatograph/mass spectrometer (GC/MS), whereby the spectrum is represented a matrix of GC/MS data; factoring the data matrix into the product orthogonal scores vectors, representing mass spectral space, and orthonormal loading vectors, representing chromatographic space, using Principal Component Analysis (PCA); and rotating the PCA solution to provide more realistic factors. In general, the pseudorank of the PCA solution can be selected to represent the number of chemically meaningful species in the sample. During the phase of acquiring the m/z spectrum, selective ion depletion of peaks can be used to eliminate one or more dominant species in the sample. Prior to factorization, the GC/MS data can be scaled so that it approximates the assumptions in the PCA factorization. The rotated PCA solution can be further refined, for example using constrained alternating least squares, to provide even more realistic mass spectral and chromatographic factors.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Figure 1:
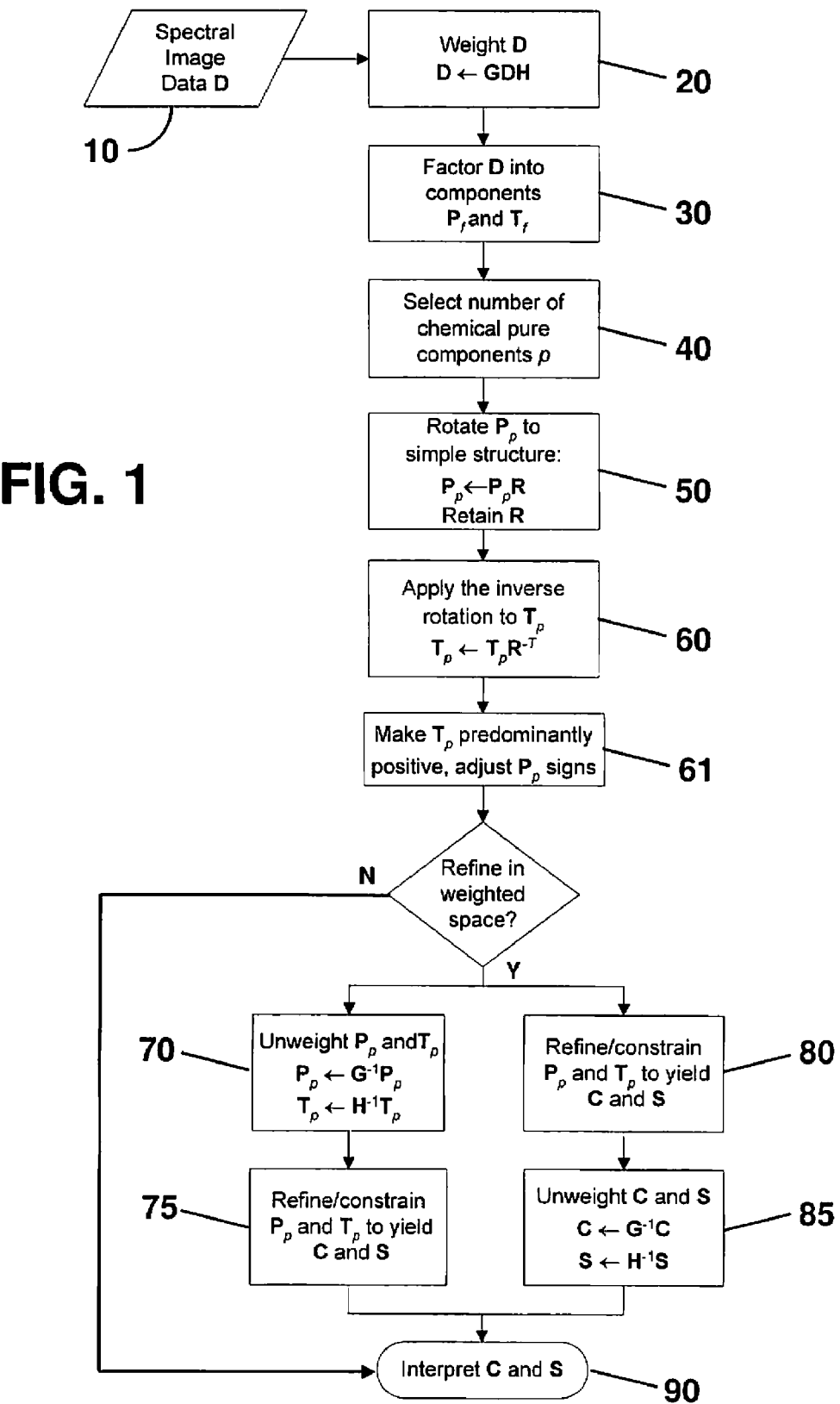
FIG. 1 is a flow diagram for a method for spectral image analysis by exploiting spatial simplicity for the case that the spectral image approximates perfectly simple structure.

In general, an image can comprise any arbitrary, multidimensional array of points. The image can include a spatial dimension, such as lines, traditional 2D images, or 3D volumes; or a temporal dimension, such as a time series of images. For example, in the case of Energy Dispersive X-ray (EDS) images, the spatial dimension is a 2D pixel array. In the case of a GC/MS image, the temporal dimension is a separation coordinate. The description that follows will begin with a description of a generalized multivariate image analysis method as applied to a spatial dimension. This generalized method is described more fully in U.S. application Ser. No. 11/233,223, which is incorporated herein by reference. This general description is then followed by a detailed description of an application of the method to the factor analysis of GC/MS data, comprising a temporal dimension or chromatographic separation coordinate.

Method for Spectral Image Analysis by Exploiting Spatial Simplicity

Multivariate spectral analysis can be performed on a full spectrum image that can be represented as a two-dimensional data matrix D. The two-dimensional data matrix D can be obtained by unfolding a measured multidimensional spectral data set. For example, the multidimensional spectra data set can be a data cube that comprises a 1D spectrum at each pixel on a 2D spatial grid corresponding to the (X,Y) coordinates of the pixel's location. The 2D data matrix D enables the easy and efficient use of standard linear algebra and matrix operations.

The data matrix D can be factored into the product of two matrices, C and $S^T$, according to Eq. (1), where D has dimensions of m×n, and m is the number of pixels and n is the number of spectral channels. The matrix C is a concentration matrix, which is related to the concentration of the chemical phases (e.g., a matrix representing a map of the pure-component abundances) and has dimensions of m×p, where p is the number of pure components. The matrix S is a spectral shapes matrix, which contains information about the spectral shapes of the pure chemical components (e.g., a matrix of the pure-component spectra). S has dimensions n×p.

The factorization of Eq. (1) can be accomplished by an image analysis of D. A number of prior image analysis methods are described in U.S. Pat. Nos. 6,584,413 and 6,675,106 to Keenan and Kotula, which are incorporated herein by reference. A spectral-image factorization method based on PCA has also been described. See M. R. Keenan and P. G. Kotula, *Surf. Interface Anal.* 36, 203 (2004), which is incorporated herein by reference.

If desired, the measured data matrix D can be weighted, depending on the type of experiment being analyzed, and depending on the properties of the noise or background signal generated during data acquisition. Weighting is generally used whenever the properties of the noise are not uniform throughout the measurement space (i.e., heteroscedastic noise). This is particularly true in the case of "counting" experiments in which the noise is characterized as following a Poisson probability distribution in which the magnitude of the uncertainty varies with the magnitude of the signal. For multi-channel data acquisition the noise is not characterized by a single probability distribution, but rather, by a distribution whose parameters will, in principle, differ from channel to channel and from pixel to pixel within a channel. Additionally, heteroscedasticity can also arise from other effects, e.g., non-uniform detector responses, or mathematical transformations applied to the data (e.g., taking logarithms).

Weighting is also useful when there is a large disparity between the total number of counts (e.g., observations) arising from different elements or phases (e.g., a sample comprising a small amount of contaminant located on top of a substrate made of a single material). Weighting, therefore, is useful for accurately identifying minor phases, trace elements, or subtle gradients in composition across a sample. By properly accounting for experimental noise characteristics, chemically relevant features having small numbers of counts can become more significant, in a least squares sense, than large magnitude noise associated with major spectroscopic features.

Therefore, data matrix D can be weighted to create a weighted data matrix $\tilde{D}$, according to $$\tilde{D}=GDH \quad (3)$$

where G is a pre-multiply weighting matrix having dimensions m×m; and H is a post-multiply weighting matrix having dimensions n×n. In general, G is used to weight the row-space of D, and H is used to weight the column-space of D. Obviously, the weighting matrices G and H can be the identity matrix if no weighting is desired.

The matrix G can be used to account for unequal variance in the observations from pixel to pixel, independent of channel number (i.e., energy or wavelength). For example, weighting by G could be used in the case where there are hot or dead pixels, or if there was an array detector where different detector elements had different noise properties. Weighting by G also could be used in the situation where there were much higher total counts in some pixels as compared to others, caused, for example, by unequal dwell times. The matrix H can account for unequal variance in the observations from channel to channel, independent of pixel location. For example, weighting by H could be used when the noise level varies from one energy channel to the next.

Spectral image analysis of the weighted data matrix $\tilde{D}$ yields $\tilde{C}=GC$, which is the weighted concentration matrix, and $\tilde{S}^T=S^TH$, which is the weighted spectral shapes matrix. The corresponding unweighted concentrations and spectra can be recovered as $C=G^{-1}\tilde{C}$ and $S^T=\tilde{S}^TH^{-1}$, respectively. For simplicity, the analysis of the unweighted data matrix D will be described hereinafter, although it will be understood that the method of the present invention can also be applied to the weighted data matrix.

Spectral Image Analysis by PCA

PCA is one of the core techniques of multivariate statistical analysis and it has been employed in numerous and diverse applications including dimensional reduction, data compression, exploratory data analysis, factor analysis, pattern recognition, classification, and multivariate calibration. In particular, PCA can be used in the analysis of hyperspectral image data. See P. Geladi and H. Grahn, *Multivariate Image Analysis*, Wiley, Chinchester, UK (1996).

The goal of PCA is to extract the useful information in a high-dimension data set into a lower dimension subspace. From a geometric point of view, PCA begins by finding that single direction in the n-dimensional space that best describes the location of the data. The vector describing that direction is the first principal component. Once found, a second direction, orthogonal to the first, is determined that best accounts for the variation in the data that is orthogonal to the first. This is the second principal component. The process continues with each new principal component maximally accounting for the variation in the data that is orthogonal to all preceding components. The first few principal components will contain the chemical information of interest. If there are p such principal components, the remaining n−p principal components are assumed to describe experimental noise or error. Limiting further analysis to the p-dimensional subspace defined by the first p principal components provides the desired dimensional reduction and data compression.

In matrix terms, PCA is concerned with factoring a data matrix D into the product of two other matrices, a scores matrix T whose columns are mutually orthogonal and a matrix P of orthonormal loading vectors, according to $$D=TP^T \quad (4)$$

To take a spectroscopic example, the loading vectors P describe the spectral characteristics of the chemical constituents of a sample and the scores T are related to their concentrations. The data set is then seen to be described as a linear combination of basis spectra. An alternative point of view can be obtained by performing PCA on the transposed data matrix $D^T$:

$$D^T=\overline{T}\overline{P}^T \quad (5)$$

In this case, the orthonormal loading vectors $\overline{P}$ describe the spatial or abundance characteristics of the data and the scores $\overline{T}$ are related to the spectra. The data is now being represented as a linear combination of basis images. These two approaches are dual and the respective loading vectors span the same space, namely, that of the spectral data.

The close connection between these two points of view can be made apparent by considering singular value decomposition (SVD) of the data, a method that is often used to compute PCA. SVD performs the factorization $$D=U\Sigma V^T \quad (6)$$

If D is an m×n matrix, then U and V are m×m and n×n orthogonal matrices, respectively, and Σ is an m×n diagonal matrix containing the singular values along the diagonal, ordered by decreasing size. The right singular vectors V provide abstract representations of the spectra of the individual chemical components (e.g., elements or phases). The min(m, n) singular values are related to the amount of variance in the data that is accounted for by the corresponding principal components. Specifically, the $i^{th}$ singular value is equal to the square root of the variance accounted for by the $i^{th}$ principal component. The diagonal form indicates that the transformed data are uncorrelated. By decomposing the data into a set of uncorrelated factors of decreasing statistical significance, data compression can be accomplished by selecting those factors having the greatest statistical significance and discarding the rest as noise or error.

SVD has the useful property that the space spanned by the first p columns of V represents, in a least squares sense, the best rank-p approximation to the space spanned by the rows of D. The remaining n−p columns of V represent experimental noise or error and can be discarded. Thus, the scores and loading matrices can be truncated, or compressed, to contain only those vectors corresponding to significant singular values. Letting $V_p$ be the matrix whose columns are the first p columns of V, a p-component PCA model can then be computed, according to $$P_p = V_p \qquad (7)$$
$$T_p = (U\Sigma)_p$$

where the columns of $P_p$ are mutually orthonormal and those of $T_p$ are mutually orthogonal. Similarly, the space spanned by the first p columns of U represents, in a least squares sense, the best rank-p approximation to the space spanned by the columns of D. The remaining m−p columns of U represent experimental noise or error and can be discarded. Thus, an alternative PCA factorization of D is $$\overline{P}_p = U_p \qquad (8)$$
$$\overline{T}_p = (V\Sigma)_p$$

where, again, the columns of $\overline{P}_p$ are mutually orthonormal and those of $\overline{T}_p$ are mutually orthogonal. Transposing Eq. (6) and comparing with Eq. (5) shows the mathematical equivalence of the dual factorizations:

$$D^T = V\Sigma U^T = (V\Sigma)U^T = \overline{T}\overline{P}^T \qquad (9)$$

In the following discussion, the bars will be dropped for clarity and the loading matrix P will represent vectors that are orthonormal in the spatial domain, unless otherwise noted.

The conclusion that arises from the foregoing discussion is that there are two equivalent and equally valid ways to describe the data matrix D in terms of a PCA model. In the picture provided by Eq. (7), the orthonormal basis is spectral in nature, whereas, the model in Eq. (8) has an orthonormal image basis. The difference between the two points of view is subtle but has major implications. These relate to how properties of orthogonal and orthonormal (i.e., orthogonal and normalized to unit length) vectors differ upon rotational transformation, as will be described below.

Rotating the PCA Solution

While the matrices T and P include all of the information contained in the pure components, they do not do so in a chemically recognizable form. Therefore, a single principal component will not, in general, represent either a pure element or a multi-element phase, but rather, a linear combination of such elements or phases. In other words, there may not be a one-to-one correspondence between a selected principal component and a particular chemical phase or pure element. For example, physically admissible concentrations must be non-negative, and the pure-component spectra must be greater than the background signal, whereas a general principal component analysis need not be thus constrained. The principal components produced by PCA often have negative values, which presents a spectrum that is difficult for the practicing analyst to understand. Additionally, a major disadvantage of PCA is that the principal components are constrained to be orthogonal, while any chemical phase that contains overlapping spectral peaks or non-specific spectral backgrounds will necessarily be non-orthogonal. Therefore, subsequent post-processing of results obtained from PCA is useful for transforming the abstract principal components into physically meaningful pure components.

Transformation or "rotation" of PCA loading vectors has been commonly employed, particularly in the psychometric community, to obtain more readily interpretable factors. See H. H. Harman, *Modern Factor Analysis,* 3rd Revised ed., The University of Chicago Press, Chicago (1976); M. W. Browne, *Multivariate Behavioral Research* 36, 111 (2001); and M. Forina et al., *J. Chemometrics* 3, 115 (1988). The general goal of such procedures is to "rotate the factors to simple structure." Thus, given a matrix of loading vectors P, a rotation matrix R is sought such that the rotated loadings $\underline{P}$=PR are in some sense simpler and hopefully easier to interpret that the original loadings. As is amply demonstrated by the references, many definitions of "simple structure" have been proposed in the literature, and many algorithms are available to determine R such that the simplicity of P is maximized. At a very basic level, however, simplicity just means that there are many zeros in the matrix of loading vectors P. A matrix that has perfectly simple structure is one that has one and only one non-zero entry in every row of the matrix.

In the area of spectral image analysis, rotation of the spectral principal components has been used to obtain simpler spectra that may be easier to interpret. Conversely, the present invention uses rotation of the spatial-domain loading vectors to obtain better, more interpretable components in the spectral domain. Accordingly, a rotation matrix R can be determined, for instance, by the Varimax procedure, that maximizes the simplicity of P. The inverse rotation can then be applied to the scores matrix T to yield a factor model that fits the original data equally as well as the PCA model. Assuming R is an orthogonal matrix (i.e., a true rotation), then $$D = TP^T = TRR^T P^T = (TR)(PR)^T = \underline{T}\underline{P}^T \text{ (spectral basis)} \qquad (10)$$

$$D = PT^T = PRR^T T^T = (PR)(TR)^T = \underline{P}\underline{T}^T \text{ (spatial basis)} \qquad (11)$$

Interestingly, while the columns of the rotated loading matrix $\underline{P}$, like those of the original loading matrix P, are mutually orthonormal, the columns of $\underline{T}$ have lost the orthogonality present in the original scores matrix T. The implication of this result is that rotation allows the spatial and spectral orthogonality imposed by PCA to be relaxed in either the spatial domain through Eq. (10) or in the spectral domain via Eq. (11).

The key observation, now, is that while spectra are rarely orthogonal, that is, pure-component spectra typically overlap either one another or non-specific backgrounds, samples are often relatively orthogonal in a spatial sense. For example, in a sample with discrete chemical phases X and Y, and assuming boundary pixels make up a small fraction of the total, any particular pixel is likely to represent either phase X or phase Y, but not both. This observation suggests that the factorization approach indicated by Eq. (11) will be effective for the spectral image analysis of a large and important class of analytical problems having spatially simple structure (i.e., substantially comprising pure pixels).

Refining the Rotated PCA Solution

As demonstrated by the foregoing discussion regarding spatially simple samples, excellent spectral estimates can be achieved by first rotating spatial-domain loading vectors to simple structure and then applying the same rotation (for the case of an orthogonal R) to the scores matrix. The pure-component concentration estimates, on the other hand, are still constrained to be orthogonal, which can introduce bias into the results if the samples are not perfectly simple. Frequently, these biases can be compensated by imposing additional constraints, non-negativity for instance, on the derived components subsequent to factor rotation. Further exclusion of bias requires that refinements be made to both the rotated spectral and spatial components. This refinement can be accomplished using algorithms that impose additional constraints. Typically, the refinement requires an iterative algorithm. Small changes in the spatial-domain components will induce changes in the spectral-domain estimates, which induce additional changes in the spatial components, and so on. For example, the refinement can be accomplished using an alternating least squares algorithm. Alternatively, a particularly suitable family of algorithms for the case of non-negative concentrations and spectra is the maximum-likelihood-based, non-negative matrix factorization (NNMF) method, which has been further elaborated for Poisson data. See D. D. Lee and H. S. Seung, *Nature* 401, 708 (1999), and P. Sajda et al., *Proc. of the SPIE, Wavelets: Applications in Signal and Image Processing X* 5207, 321 (2003).

Method for Spectral Image Analysis by Exploiting Spatial Simplicity

In FIG. 1 is shown a method for spectral image analysis by exploiting spatial simplicity using PCA, as described above. At step 10 is provided a two-dimensional matrix of spectral image data D. The 2D matrix D can be obtained by unfolding a measured multidimensional spectral data set. Alternatively, the data matrix D at step 10 can be represented as an arbitrary factor model, according to $$D = AB^T \quad (12)$$

where the data factor matrix A comprises spatial information and the data factor B comprises spectral information. At step 20, the data matrix D can be weighted to create a weighted data matrix, according to Eq. (3). For ease of description, the resulting weighted data matrix $\tilde{D}$ can be assigned to data matrix D (as indicated by the ← arrow).

PCA can be performed on either the unfactored data matrix D, according to Eq. (4), or the transposed unfactored data matrix $D^T$, according to Eq. (5), using a factorization algorithm. The data matrix is thereby factored into the product of a scores matrix T, whose columns are mutually orthogonal, and a matrix P of orthonormal loading vectors. As is well known to those having skill in the art, there are many algorithms that can be used to perform the PCA factorization, including nonlinear iterative partial least squares (NIPALS), eigenanalysis, and SVD. The PCA will yield a very large number of principal components. In general, the number of principal components representing noise greatly outnumbers the chemically relevant principal components. Therefore, the f most significant components (e.g., corresponding to the f most significant eigenvalues or singular values) are selected. It is not necessary to know exactly how many significant components f are needed to represent the chemical information, only that the number of f most significant components selected equals or exceeds the number of chemical pure components p in the sample (i.e., f>p). See R. Bro and C. Andersson, *Chemometrics and Intell. Lab. Syst.* 42, 105 (1998). Accordingly, at step 30, the loading and scores matrices P and T can be truncated to matrices $P_f$ and $T_f$ by retaining only those vectors corresponding to the f most significant components.

At step 40, the number of pure components p can be selected to provide a loading matrix $P_p$ having mutually orthonormal columns and a scores matrix $T_p$ having mutually orthogonal columns. The appropriate number of pure components p can be estimated, for instance, using the eigenanalysis as described by Keenan and Kotula.

At step 50, an orthogonal rotation matrix R can be determined. For example, the rotation matrix R can be determined by one of the Orthomax-family of procedures (e.g., Quartimax or Varimax). The rotation matrix R can be applied to the loading matrix $P_p$ to provide a rotated loading matrix $\tilde{P}_p$ having a maximally simple structure, according to $\tilde{P}_p = P_p R$. For ease of description, the rotated loading matrix $\tilde{P}_p$ can be assigned to the loading matrix $P_p$.

At step 60, the inverse rotation can be applied to the scores matrix $T_p$ to provide a rotated scores matrix $\tilde{T}_p$, according to $\tilde{T}_p = T_p R^{-1}$. For ease of description, the rotated scores matrix $\tilde{T}_p$ can be assigned to the scores matrix $T_p$. The data matrix D is thereby described in the spatial basis $\underline{P}$, according to Eq. (11).

While the rotated loading matrix is maximally simple, the signs of the rotated principal components suffer a sign ambiguity. In the approximately perfectly simple case, the elements of a given score vector (i.e., a column of $T_p$) will be either predominantly negative or predominantly positive. Since we desire non-negative spectral components, the columns of $T_p$ that are predominantly negative along with the corresponding columns of $P_p$ are multiplied by −1 at step 61.

If no refinement of the rotated PCA solution is necessary, the loading vectors matrix can be normalized and assigned to the concentration matrix (i.e., C←$P_p$) and the scores matrix can be normalized and assigned to the spectral shapes matrix (i.e., S←$T_p$) and these matrices can be interpreted at step 90.

Alternatively, the rotated PCA solution can be further refined. Only the rotated loading matrix can be refined, or both the loading and scores matrices can be refined. The rotated PCA solution can be refined either prior or subsequent to unweighting. At step 70, the rotated PCA solution can be unweighted prior to refinement by recovering the unweighted loading matrix and unweighted scores matrix using the inverse of the pre- and post-multiply weighting matrices, according to $P_p \leftarrow G^{-1} P_p$ and $T_p \leftarrow H^{-1} T_p$. Obviously, the inverse weighting matrices $G^{-1}$ and $H^{-1}$ can be the identity matrix, if the data matrix was not weighted at step 20. At step 75, the unweighted PCA factors $P_p$ and $T_p$ can then be refined, yielding the concentration and spectral shapes matrices C and S. Alternatively, the weighted PCA solution can be refined first at step 80 to yield the weighted concentration and spectral shapes matrices, and then these matrices can be unweighted at step 85, according to C←$G^{-1}$C and S←$H^{-1}$S.

Figure 2:
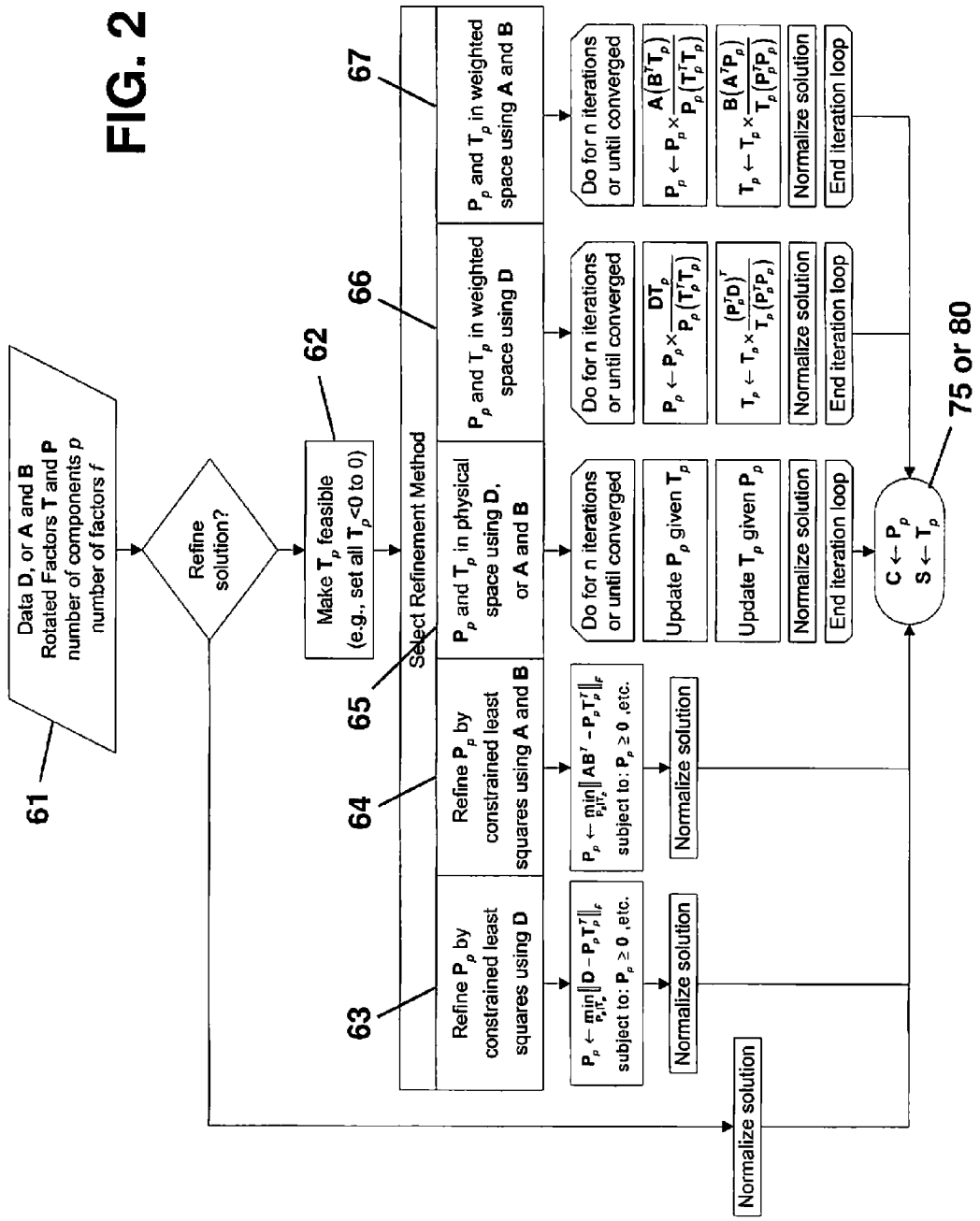
FIG. 2 is a flow diagram of various approaches to refinement of the PCA solution.

In FIG. 2 are shown a number of methods for refining either the weighted PCA factors $P_p$ and $T_p$ at step 80 or the unweighted PCA factors $P_p$ and $T_p$ at step 75, depending on whether the full data matrix D or the factored representation, A and B, is used for refinement. Component refinement is accomplished by forcing the spectral and abundance components to satisfy physically motivated constraints. For example, physically admissible concentrations and spectra must typically be non-negative. The matrix R was obtained at step 50 by rotating the loading matrix $P_p$ to simple structure for the purpose of obtaining physically realistic and easily interpretable spectral pure components $T_p$ in steps 60 and 61. At step 62, the initial estimate $T_p$ can be made feasible by ensuring that no elements violate the constraints, for instance, by setting the remaining negative matrix elements to zero. Next, as described below, either the spatial or both the spatial and spectral rotated components can be further refined to exclude bias by using algorithms that impose additional constraints.

Step 63 shows a constrained-least-squares approach (e.g., MCR-ALS) to refine either the unweighted rotated loading matrix (i.e., at step 75), or the weighted rotated loading matrix (i.e., at step 80), using the data matrix D. The refined loading matrix $P_p$ can be computed from the data and the feasible estimate for the scores matrix $T_p$ by least squares, subject to constraints, according to $$P_p \leftarrow \min_{P_p|T_p} \|D - P_p T_p^T\|_F \quad (13)$$

A common constraint is non-negativity (i.e., $P_p \geq 0$). The refined PCA solution can then be normalized and assigned to the concentration matrix (i.e., $C \leftarrow P_p$) and the spectral shapes matrix (i.e., $S \leftarrow T_p$) at step 75 or 80. If the resulting concentration and spectral shapes matrices C and S are weighted, they can be unweighted at step 85.

Alternatively, at step 64, if the data matrix is represented as an arbitrary factor model (i.e., as $AB^T$) the refined rotated loading matrix can be computed, subject to constraints, according to $$P_p \leftarrow \min_{P_p|T_p} \|AB^T - P_p T_p^T\|_F \quad (14)$$

If the rotated PCA factors have been unweighted at step 70, a refined factorization including refined estimates of both $P_p$ and $T_p$ can be computed, in general, using an alternating sequence of conditional refinements with the data matrix D, according to step 65. One specific refinement algorithm is based on constrained alternating least squares. Given an initial feasible estimate for the scores matrix $T_p$, an updated $P_p$ can be computed, subject to constraints, according to $$P_p \leftarrow \min_{P_p|T_p} \|D - P_p T_p^T\|_F \quad (15)$$

Given this updated $P_p$, an updated $T_p$ can be computed, subject to constraints, according to $$T_p \leftarrow \min_{T_p|P_p} \|D - P_p T_p^T\|_F \quad (16)$$

The updated PCA factors can be normalized and Eqs. (15) and (16) can be iterated for a predetermined number of iteration loops or until an acceptable level of convergence is achieved. The refined PCA solution can then be assigned to the concentration and spectral shapes matrices at step 75. A similar refined PCA factorization can be computed if the data matrix is represented as an arbitrary factor model.

Another refinement algorithm, at step 65, for the case of Poisson data is the constrained non-negative matrix factorization algorithm of Sajda et al. The Sajda algorithm naturally imposes non-negativity constraints and is suitable for count data.

Steps 66 and 67 show alternative refinement approaches based on the NNMF algorithm of Lee and Seung. This method iteratively updates the non-negative rotated PCA factors under the assumption of uniform Gaussian noise. For heteroscedastic data, these algorithms are appropriately applied in the weighted space.

At step 66, a refined weighted PCA factorization can be computed using the data matrix D. Given an initial feasible estimate for the scores matrix $T_p$, the loading matrix $P_p$ can be updated, according to $$P_p \leftarrow P_p \times \frac{DT_p}{P_p(T_p^T T_p)} \quad (17)$$

Given this updated $P_p$, an updated $T_p$ can be computed, according to $$T_p \leftarrow T_p \times \frac{(P_p^T D)^T}{T_p(P_p^T P_p)} \quad (18)$$

The updated PCA factors can be normalized and Eqs. (17) and (18) can be iterated for a predetermined number of iteration loops or until an acceptable level of convergence is achieved. The refined PCA solution can then be assigned to a weighted concentration matrix (i.e., $C \leftarrow P_p$) and a weighted spectral shapes matrix (i.e., $S \leftarrow T_p$) at step 80. These weighted matrices can be unweighted at step 85, according to $C \leftarrow G^{-1}C$ and $S \leftarrow H^{-1}S$.

Alternatively, at step 67, a refined weighted PCA factorization can be computed using a pre-factored data matrix $AB^T$. Given $T_p$, an updated $P_p$ can be computed, according to $$P_p \leftarrow P_p \times \frac{A(B^T T_p)}{P_p(T_p^T T_p)} \quad (19)$$

With this updated $P_p$, an updated $T_p$ can be computed, according to $$T_p \leftarrow T_p \times \frac{B(A^T P_p)}{T_p(P_p^T P_p)} \quad (20)$$

The updated PCA factors can be normalized and Eqs. (19) and (20) can be iterated for a predetermined number of iteration loops or an acceptable level of convergence is achieved. The refined PCA solution can then be assigned to a weighted concentration matrix (i.e., $C \leftarrow P_p$) and a weighted spectral shapes matrix (i.e., $S \leftarrow T_p$) at step 80. These weighted matrices can be unweighted at step 85, according to $C \leftarrow G^{-1}C$ and $S \leftarrow H^{-1}S$.

Method for Factor Analysis of GC/MS Data

Hyphenated chromatographic methods are some of the most powerful techniques for analysis of mixtures available. See G. Cudiamat, GC-MS, *E-Separation Solutions*; Advanstar Communications, Inc.: Woodland Hills, Calif., http://chromatographyonline.findanalytichem.com/lcgc/Research/GCndashMS/ArticleStandard/Article/detail/623723, (retrieved 2 Nov. 2009). Gas chromatography coupled with mass spectrometry (GC/MS) is one of the most widely utilized methods for the analysis of volatile species. A very powerful technique for improving the selectivity and signal to noise ratio (SNR) of GC/MS is selected ion monitoring (SIM). See D. A. Skoog and J. J. Leary, *Principles of Instrumental Analysis*; Saunders College Publishing: Fort Worth (1992). SIM works by limiting the mass spectral filter to those ions associated with a chemical species of interest. See C. G. Herbert and R. A. W. Johnstone, *Mass Spectrometry Basics*; CRC Press: Boca Raton, Fla. (2003). It can produce spectacular results when the analysis is limited to a few species. However, when the analysis is intended to find minor or unknown species in a mixture, use of SIM could result in missing important information.

There have been numerous methods developed to analyze GC/MS data over the years. One early method focused on identifying m/z indices which represented the pure chromatogram of each chemical component. See J. E. Biller and K. Biemann, *Analytical Letters* 7, 515 (1974). Knorr et al. took a different tack by modeling chromatogram peaks as skewed Gaussian functions while using a SIMPLEX minimization. See F. J. Knorr et al., *Anal. Chem.* 53, 821 (1981). Various modifications and advancements of the first theme have led to a very popular and versatile approach, which has become known as AMDIS. See R. G. Dromey et al., *Anal. Chem.* 48, 1368 (1976); B. N. Colby, *J. Am. Soc. Mass Spectrom.* 3, 558 (1992); S. E. Stein, *J. Am. Soc. Mass Spectrom.* 10, 770 (1990); and W. G. Mallard and J. Reed, "Automated Mass Spectral Deconvolution & Identification System AMDIS—USER GUIDE"; National Institute of Standards and Technology (NIST): Gaithersburg, Md. (1997). These approaches use the mass spectral information as well as assumptions about peak shape to "deconvolute" the chromatogram.

Factor analysis methods that assume no analytic model of the character of the data are often called soft models or matrix-based methods. Such self modeling methods typically make only limited assumptions about the nature of the data, but impose constraints such as non-negativity to achieve physically meaningful results. Alternating least squares (ALS) or alternating regression (AR) methods have been employed successfully in GC/MS analysis. See E. J. Karjalainen et al., *Advances In Mass Spectrometry*, Vol. 14; E. J. Karjalainen et al., Eds.; Elsevier: Amsterdam, The Netherlands, pp 595-609 (1998). Unfortunately, that algorithm was initiated with random starting points, which can lead to solutions trapped in local minima.

Analysis of forensic samples presents a case where the identification of minor or unsuspected chemical species is very important. Minor components may present themselves as evidence of the source of a compound used in a criminal activity, such as an accelerant in arson or a byproduct from production of material used in a chemical attack. Separating the small but important components from a solvent or a dominant agent can be critical to identifying the source of the material. In the case of GC/MS, identifying minor components can be quite a challenge when the data are dominated by solvents or the major components, which may even saturate the column and/or detector.

Figure 3:
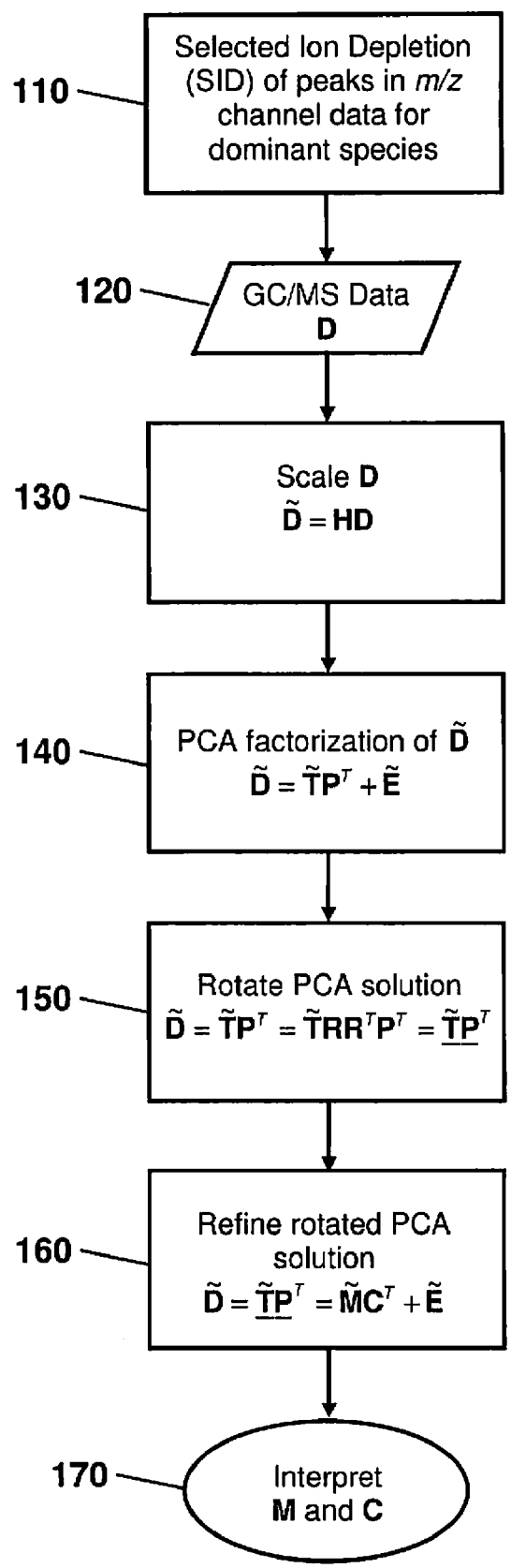
FIG. 3 is a flow diagram of a method for factor analysis of GC/MS data.

In FIG. 3 is shown a flow diagram for the method of the present invention. The method applies the general method for spectral image analysis by exploiting spatial simplicity, described above, to the factor analysis of GC/MS data, wherein a temporal dimension or chromatographic separation coordinate replaces the spatial coordinate. The factor analysis method takes special advantage of the simple character of GC/MS data. A chromatogram is "simple" in the sense that it consists of relatively discrete elution peaks that represent separated chemical species. The method of the present invention exploits this simplicity in the temporal domain to make the resulting factor model more realistic. The method is fast, reasonably straightforward and easy to apply.

The method can begin with measuring a mass-charge (m/z) spectrum of a sample with a gas chromatograph/mass spectrometer (GC/MS) at step 120. The spectrum can be represented an m×n matrix of GC/MS data D, wherein m is a number of mass spectra and n is a number of eluted chromatographic peaks.

An alternative embodiment of the method enables a rapid analysis of GC/MS data containing large, interfering solvent peaks. The embodiment relies on extracting information on minor components while reducing the impact of dominant components is the mass-spectral information originating from dominant species is ignored using the technique of selected ion depletion (SID).

Selected Ion Depletion of GC/MS Data

Selected ion monitoring is a technique that is implemented in the data acquisition phase of an experiment. It is accomplished by tuning the mass spectrometer to a suitable mass-charge (m/z) value or set of values and acquiring the current(s) as counts as a function of elution time. See D. A. Skoog and J. J. Leary, *Principles of Instrumental Analysis*, Saunders College Publishing: Fort Worth (1992). In this way, the mass spectrometer becomes a very effective mass filter with high SNR at the expense of mass spectral range. By contrast, with selective ion depletion the mass spectrometer is scanned continually over an applicably wide m/z range sufficient to capture all of the fragments that one could reasonably expect in the sample. This may be seen as a more traditional, if brute force, method of obtaining data, where a larger range of m/z is collected at the expense of SNR. The advantage of collecting the full mass spectral range is that one has access to all mass fragments, which may include information on unexpected chemical species.

Often, chromatographic data contain peaks from dominant species or solvent that may be saturated either in the chromatographic domain or the mass spectral domain. Saturation, or overloading, in the chromatographic domain is frequently manifested as a distorted, non-Gaussian shaped peak with excessive tailing. See C. F. Poole and S. K. Poole, *Chromatography Today*, Elsevier Science: Amsterdam, The Netherlands (1991). Saturation in the mass spectral domain can be recognized as distorted mass spectra across the chromatographic peak, with the most populated mass channels saturating, resulting in reduced relative ratios to unsaturated peaks. These effects can make factor analysis more difficult by obscuring small peaks and increasing the complexity of the data. As intensity of the saturated peaks no longer increases with concentration, they are highly non-linear and thus linear factor analysis methods fail to produce easily interpretable results. A solution for this type of problem is to remove the m/z channel data for major components and solvents via SID during the acquisition phase, as shown at step 110, to provide the matrix D of measured GC/MS data at step 120.

Scaling of GC/MS Data

Preferably, prior to performing factor analysis, the GC/MS data 120 can be appropriately scaled (weighted) at step 130 so that it approximates the assumptions of the factor analysis method. The factor analysis method of the present invention can use least squares, which assumes that the errors are independently and identically distributed (i.i.d.) normal. Since these GC/MS data are collected as counts from a quadrupole mass spectrometer, the first principles assumption is that the data are actually Poisson distributed. See C. Hackett et al., *J. Electron. Mater.* 28, 774 (1999); I. S. Begley and B. L. Sharp, *J. Anal. At. Spectrom.* 12, 395 (1997); and B. El Abbassi et al., *Int. J. Mass Spectrom. Ion Processes* 141, 171 (1995). Techniques are known for optimal scaling of multivariate Poisson-distributed data. See M. R. Keenan, *Techniques and Applications of Hyperspectral Image Analysis*, Vol.; Grahn, H. F., Geladi, P., Eds.; John Wiley & Sons, Ltd: Chichester, West Sussex, England, pp 89-126 (2007); M. R. Keenan and P. G. Kotula, *Appl. Surf. Sci.* 231/232, 240 (2004); and M. R. Keenan and P. G. Kotula, *Surf. Interface Anal.* 36, 203 (2004). Briefly, the data can be scaled using the inverse of the square root of the mean mass spectrum.

Consider some GC/MS data in the m×n matrix D oriented as mass spectral domain by chromatographic domain with mean m/z spectrum $\bar{d}_m$ given by $$\bar{d}_m = \frac{1}{n} D 1_n \qquad (21)$$

where 1 is an n-vector column of ones. The data can be scaled in D with the diagonal matrix H whose diagonal elements are $\bar{d}_m^{-1/2}$ using $$\tilde{D} = HD \qquad (22)$$

where $\tilde{D}$ is the data weighted for Poisson statistics. This scaling decreases the effect of large variations in the data due solely to noise in intense spectral regions. It is important for subsequent factor analysis as it effectively down-weights the effect of variance due to noise in intense spectral features and concomitantly up-weights minor spectral features, which in the raw data are smaller in magnitude than noise elsewhere. For the remaining discussion, it will be assumed that the data matrix D has been scaled, although scaling is not a necessary step in the method of the present invention.

Principal Component Analysis of GC/MS Data

As described above, PCA is a statistical method that decomposes a matrix into two sets of orthogonal basis vectors, ordered by decreasing variance, that model the row and column spaces of the matrix. See E. R. Malinowski, *Factor Analysis in Chemistry*; John Wiley and Sons, Inc.: New York (1991); and M. R. Keenan, *J. Vac. Sci. Technol. A* 23, 746 (2004). It is often used as an initial data reduction method, whose subspace representation may be readily factor-analyzed by additional statistical treatments. See M. R. Keenan, *Techniques and Applications of Hyperspectral Image Analysis*, Vol.; Grahn, H. F., Geladi, P., Eds.; John Wiley & Sons, Ltd: Chichester, West Sussex, England, pp 89-126 (2007).

As shown at step 140, PCA can be represented in matrix form as $$\tilde{D} = \tilde{T} P^T + \tilde{E} \qquad (23)$$

where $\tilde{T}$ is an m×p matrix which describes the column (or mass spectral) space of the scaled data in $\tilde{D}$, P is an n×p matrix describing the row (or chromatographic) space of $\tilde{D}$, $\tilde{E}$ is an m×n matrix of scaled residuals or noise, and the superscript "T" indicates the transpose of the preceding matrix or vector. p is used to define the size, or pseudorank, of the subspace model that describes the chemically meaningful information contained in $\tilde{D}$, simply put the number of distinguishable pure chemical species in $\tilde{D}$. $\tilde{T}$ is orthogonal and P is orthonormal having the properties:

$$\Lambda = \tilde{T}^T \tilde{T} \qquad (24)$$
$$I = P^T P$$

where I is a p×p identity matrix and $\Lambda$ is a p×p diagonal matrix of eigenvalues ordered from largest to smallest. One can also compute a "full set" of eigenvalues of length min(m, n) for fairly low computational cost. These eigenvalues can be used to estimate the pseudorank, p, in numerous ways. See E. R. Malinowski, *Factor Analysis in Chemistry*, John Wiley and Sons, Inc.: New York (1991). Commonly, a semi-logarithmic plot of eigenvalue versus factor number is produced and the number of factors selected where a "knee" occurs in the plot. See M. L. Braun, M. L. Dissertation, University of Bonn, Bonn (2005).

There is a variety of methods to compute the PCA, among these are nonlinear iterative partial least square (NIPALS), eigenanalysis, and singular value decomposition (SVD). See P. Geladi and B. R. Kowalski, *Anal. Chim. Acta* 185, 1 (1986); R. A. Johnson and D. W. Wichern, *Applied Multivariate Statistical Analysis*, Prentice Hall: Englewood Cliffs, N.J. (1992); G. H. Golub and C. F. Van Loan, *Matrix Computations*, 3rd ed.; Johns Hopkins University Press: Baltimore (1996); and R. M. Larsen, "Lanczos bidiagonalization with partial reorthogonalization"; Report Number DAIMI PB-357; Department of Computer Science—Daimi, Aarhus University: Aarhus, Denmark (1998). SVD is very convenient since it decomposes the matrix $\tilde{D}$ as $$\tilde{D} = \tilde{U} S V^T + \tilde{E} \qquad (25)$$

where U and V are, respectively, the m×p and n×p matrices of orthogonal left and right singular vectors and S is the p×p diagonal matrix of singular values. The singular values are the square roots of the eigenvalues, viz.

$$\Lambda = S^2 \qquad (26)$$

Equations (23) and (25) can be combined to show that $$\tilde{T} = \tilde{U} S \qquad (27)$$
$$P = V$$

The tilde notation indicates that the mass-spectral domain bears the scaling. Which domain is scaled is important to note, since after factor analysis these factors will be returned to their native scale, specifically $$T = H^{-1} \tilde{T} \qquad (28)$$

Rotating the PCA Solution

After performing PCA, an orthogonal, rank-p representation of the data is obtained that will probably not resemble any meaningful information to the chromatographer. Consequently, additional factor analysis is required to transform the PCA factors into interpretable factors. A reasonable approach to transforming the factors is to use a factor rotation method.

Factor rotation methods seek to maximize (or minimize) some criterion that is consistent with the nature of the data. In the case of GC/MS data, the varimax rotation is an appropriate criterion for the chromatographic domain. See R. J. Rummel, *Applied Factor Analysis*; Northwestern University Press: Evanston, Ill. (1970); H. H. Harman, *Modern Factor Analysis*; University of Chicago Press: Chicago (1976); and M. R. Keenan et al., *Proceedings of SPIE*, Seattle, Wash., USA, Jul. 8-10, 2002, SPIE—The International Society for Optical Engineering; 193 (2002). The varimax criterion seeks an orthogonal rotation matrix, R, which maximizes the row (or chromatographic) variance of the orthonormal matrix P, thereby maximizing the "simplicity" of the rotated elution-time or chromatographic factors.

As shown at step 150, a rotation matrix R can be applied, according to $$\tilde{D} = \tilde{T}P^T = \tilde{T}RR^T P^T = \underline{TP^T} \quad (29)$$

Generally, the factors of chromatographic domain are simple or sparse. For example, when a species elutes it produces a peak in the chromatogram, generating a chromatographic factor with a single peak, and zeros or noise at all other times. Unless another species co-elutes, all other factors will be zero-valued (noisy) at the elution times encompassing that species peak. So, the chromatographic domain is, generally, sparse. Overlapping due to co-elution or the presence of a large background is a violation of this premise. By contrast, there is no reason to expect that the mass-spectral domain is sparse since many different compounds generate the same mass fragments, although not in the same pattern; so this violates the simplicity assumption.

Refining the Rotated PCA Solution by MCR

If all species were to elute at different times such that none were overlapped, and no background arose from column packing loss and discharge, then PCA and varimax rotation would be sufficient to produce interpretable results. Refinement of the rotated PCA solution can be used to deal with these problems. MCR-ALS, also called linear unmixing, is a factor analysis method that utilizes an alternating least squares strategy while employing constraints; the most common constraint used being non-negativity. See M. R. Keenan et al., *Proceedings of SPIE*, Seattle, Wash., USA, Jul. 8-10, 2002; SPIE—The International Society for Optical Engineering; 193 (2002); R. Tauler et al., *Anal. Chim. Acta* 248, 447 (1991); M. H. Van Benthem et al., *J. Chemom.* 16, 613 (2002); P. G. Kotula et al., *Microsc Microanal* 9, 1 (2003); R. Bro and S. DeJong, *J. Chemom.* 11, 393 (1997); and M. H. Van Benthem and M. R. Keenan, *J. Chemom.* 18, 441 (2004).

At step 160, MCR seeks to solve $$\tilde{D} = \tilde{M}C^T + \tilde{E} \quad (30)$$

where $\tilde{M}$ is the nonnegative m×p matrix modeling the column (or mass spectral) space of the scaled data in $\tilde{D}$, C is the nonnegative n×p matrix modeling the row (or chromatographic) space of $\tilde{D}$ (note that, here M is a matrix of mass spectral factors that is equivalent to the pure component matrix C in Eq. (1). C in Eq. (30) is a matrix of chromatographic factors that is equivalent to the pure-component spectra matrix S in Eq. (1)).

As described above, one specific refinement algorithm is based on constrained alternating least squares. Given an initial feasible estimate for the scores matrix T, an updated P can be computed, subject to constraints, according to $$P \leftarrow \min_{P|T} \|D - PT^T\|_F \quad (31)$$

For example, the constraint can be a non-negativity constraint. Given this updated P, an updated T can be computed, subject to constraints, according to $$T \leftarrow \min_{T|P} \|D - PT^T\|_F \quad (32)$$

The updated PCA factors can be normalized and Eqs. (31) and (32) can be iterated for a predetermined number of iteration loops or until an acceptable level of convergence is achieved.

Combining equations (30) and (29) provides the refined PCA solution $$\tilde{D} = \underline{TP^T} = \tilde{M}C^T \quad (31)$$

which represents the dimension reduction of $\tilde{D}$ as well as the imposition of constraints on the rotated PCA factors.

Finally, following MCR, the factors in $\tilde{M}$ can be rescaled, if necessary, using the appropriate substitution into Eq. (28). At step 170, an m×p matrix M of refined mass spectral factors and an n×p matrix C of refined chromatographic factors can be interpreted for the p chemically meaningful species in the sample.

Factor Analysis of GC/MS Data

The method of the present invention is illustrated by the analysis of two data sets on standard mixtures which are highlighted by separation and identification of heavily overlapped peaks caused by an isotopic chlorine effect. Two known mixtures were analyzed. Commercially available volatile organic compound (VOC) mixtures, VOC Mix 6, and VOC Mix 8 (Supelco Inc., Bellefonte, Pa.) were analyzed as received. VOC Mix 6 contains six compounds: dichlorofluoromethane, chloromethane, vinyl chloride, bromomethane, ethyl chloride, and trichlorofluoromethane dissolved in methanol. VOC Mix 8 contains 11 compounds: trans-1,2-dichloroethylene, cis-1,2-dichloroethylene, 1,2-dichloropropane, toluene, tetra-(per)chloroethylene (PCE), chlorobenzene, ethylbenzene, p-xylene, styrene, o-xylene, 1,2-dichlorobenzene dissolved in methanol. These mixtures were analyzed using an Agilent 6890 gas chromatograph/5975N mass spectrometer equipped with a J&W DB-5 ms, 60m×0.32 mm×1.0 μm film thickness, gas chromatography column. The analytical conditions for the mixture were modified for each mixture. The GC conditions used for VOC Mix 6 were isothermal at 35° C. for 7 minutes, helium carrier gas flow rate of 1.2 mL/min, splitless injection of 0.2 μL of solution into 250° C. injector. The mass spectrometer was operated in the full scan mode from m/z: 27-120. The GC conditions used for the VOC Mix 8 were isothermal at 35° C. for 2 minutes, then ramped at 10° C./min to 200° C. and held for 2 minutes, then 20° C./min to 290° C. and held for 15 minutes. The helium carrier gas was kept at a constant flow rate of 1.4 mL/min. A splitless injection of 0.2 μL of solution into 250° C. injector was used to introduce the mixture. The mass spectrometer was operated in the full scan mode from m/z: 27-120 to the 7 minute mark, then m/z: 33-320 through 18 minutes, then finally to m/z: 33-380 through the end of the analytical run. Mass data were collected in increments of 0.1 amu, and binned to the nearest unit amu.

Factor Analysis of VOC Mix 6 Data

Figure 4:
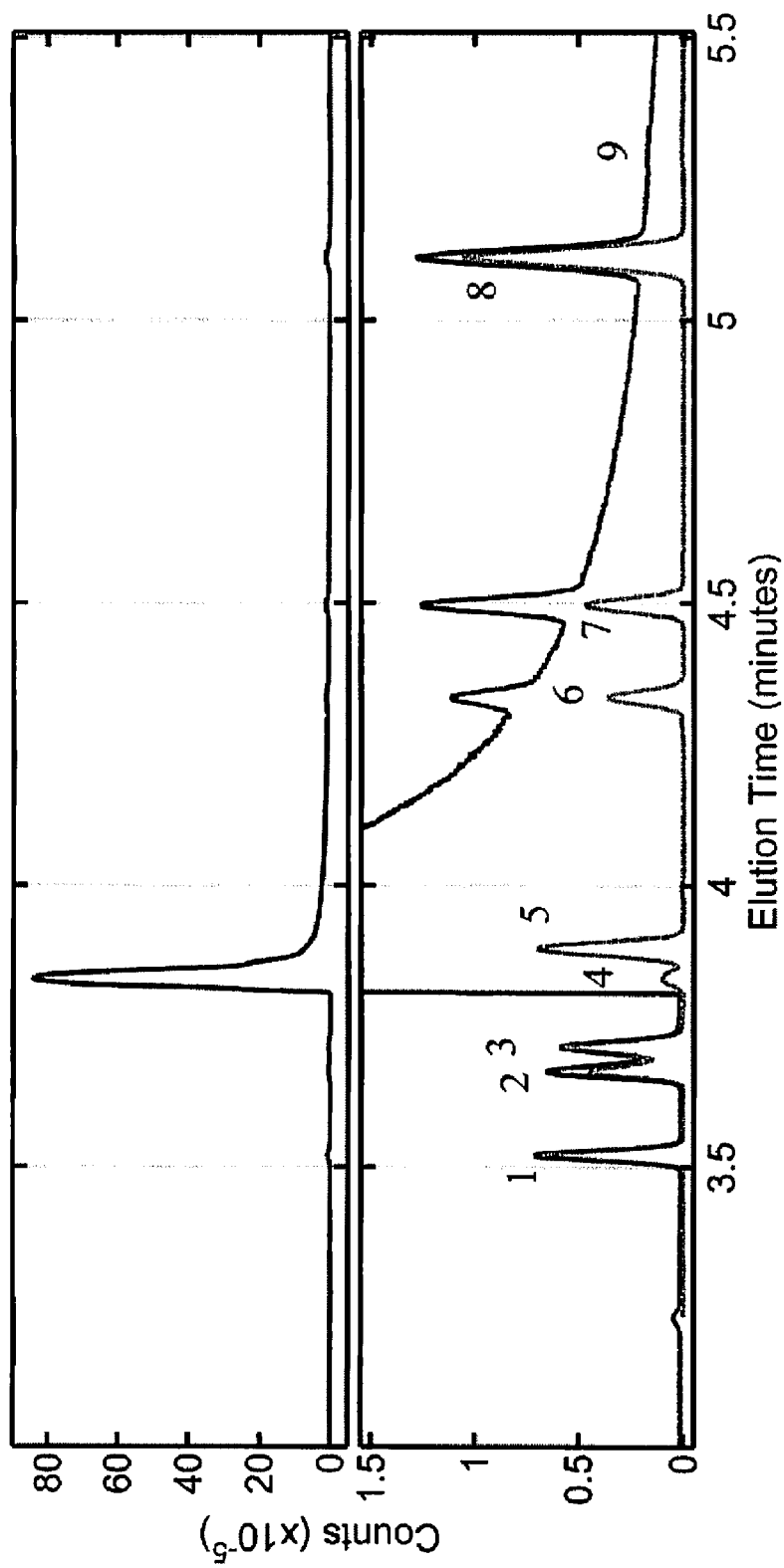
FIG. 4 shows ion chromatograms for volatile organic compound mixture VOC Mix 6. The top plot displays a VOC Mix 6 total ion chromatogram prior to data pretreatment, showing the dominance of the methanol solvent peak. The bottom plot shows the comparison of the total ion chromatograms of the raw VOC Mix 6 GC/MS data and of the same data after SID removing m/z 28-33.

The VOC Mix 6 data were collected over a time range of approximately six minutes constituting 4287 time elements. The mass spectral domain covered m/z 27-119, whose non-zero entries consisted of 65 m/z elements. An all-zero column of mass spectral values was "depleted" and not analyzed since it contained no information. The top plot in FIG. 4 is the total ion chromatogram of the raw data for VOC Mix 6; which is dominated by the methanol peak. The elution time range was truncated to a range of approximately 3-5.5 minutes to focus on the region of interest. In addition, the range m/z 28-33 represents the SID region for the methanol peak. See S. E. Stein, NIST Mass Spectrometry Data Center, *NIST Chemistry WebBook, NIST Standard Reference Database Number 69*; Linstrom, P. J., Mallard, W. G., Eds.; National Institute of Standards and Technology: Gaithersburg Md., 20899, 2008, http://webbook.nist.gov, (retrieved 24 Oct. 2009). After this modification, the data size was 741 time elements by 56 m/z elements. The bottom plot in FIG. 4 contains expanded-scale total ion chromatogram of the raw data as well as the SID plot with the methanol m/z eliminated. Most obvious here is complete loss of the methanol peak and its long tail, but an important consequence is the appearance of a peak (#4) that previously was concealed completely. Elimination of the methanol contribution is important for several reasons. Due to saturation effects, it makes the data much more complex than simply the addition of another chemical species. Its long tail complicates the analysis of overlapped peaks, since this behaves like a non-zero baseline, which prevents complete unmixing with PCA and presents special challenges for MCR.

Figure 5:
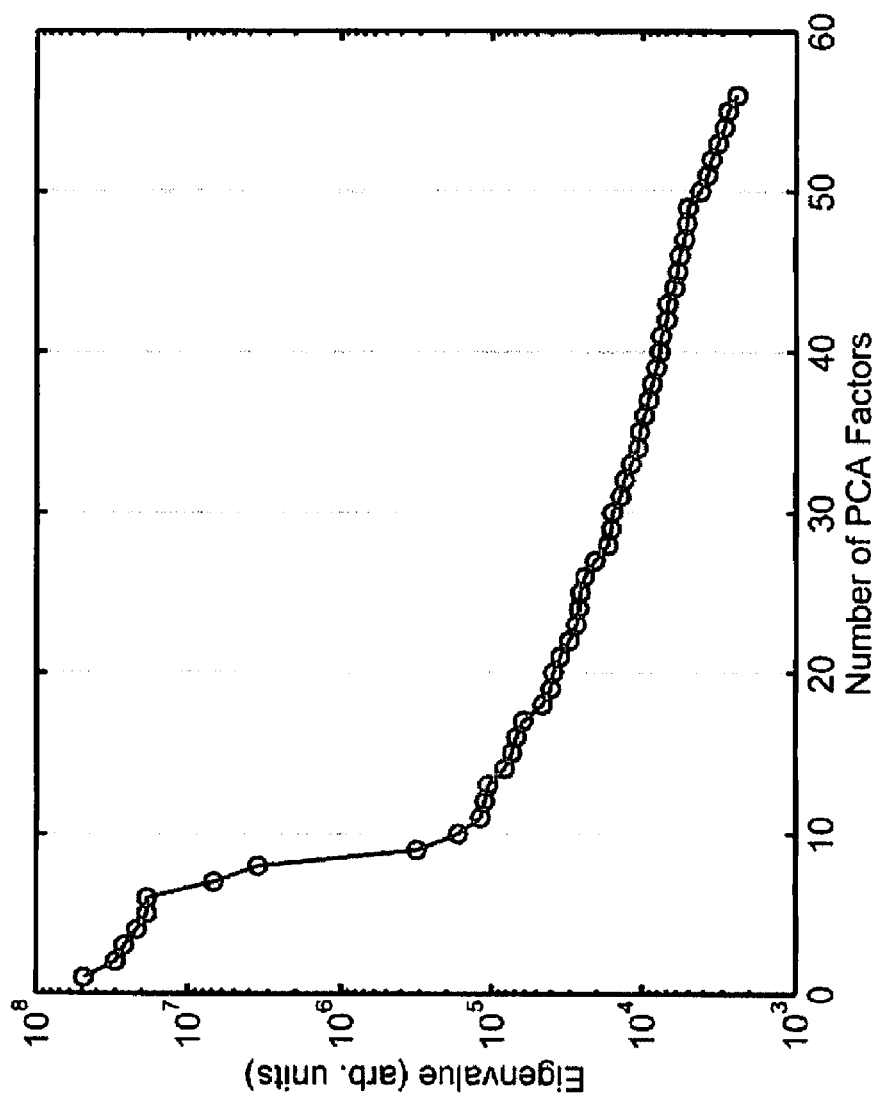
FIG. 5 is a graph of the eigenvalues of Poisson-scaled GC/MS VOC Mix 6 data plotted versus PCA factor number.

FIG. 5 is a scree plot of the eigenvalues of Poisson-scaled data VOC Mix 6. The plot shows nine or 10 significant PCA factors indicating nine or 10 possible analytes in the chromatogram. While the mixture purports to contain six species, the mixture and/or the solvent may be contaminated, or the column could have some carryover. Analyses of both ranks nine and 10 were conducted on the data. The results of the rank-nine model, constituting over 99% of the total variance, are presented below. The rank 10 analysis differs little from that of rank 9, with the additional component giving insignificant interpretive value.

Figure 6:
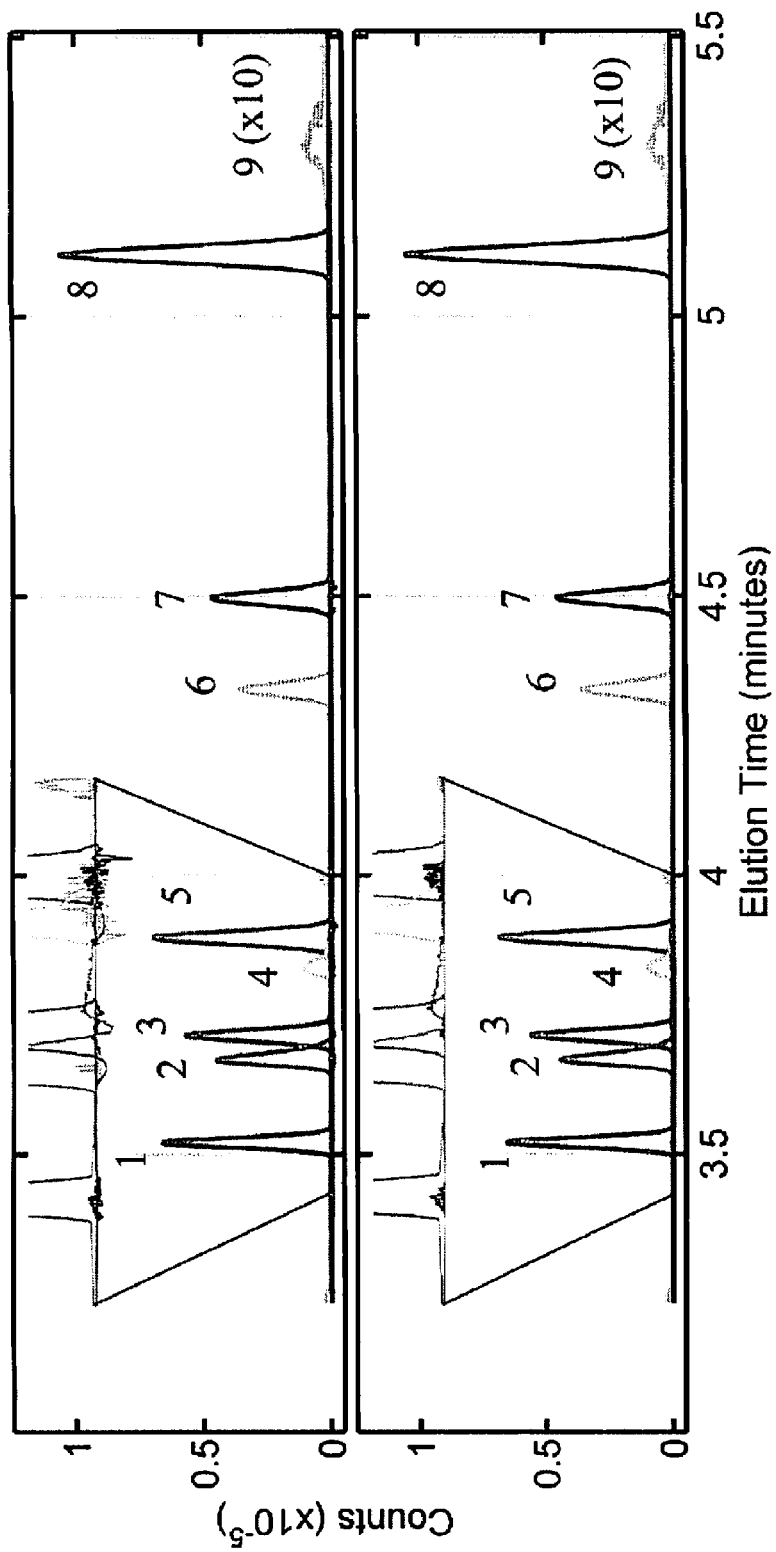
FIG. 6 shows the chromatographic factors for the rotated and refined PCA solutions for the VOC Mix 6 data. The top plot contains the eigenvectors for varimax-rotated PCA on the Poisson-scaled SID data. The plots are total ion chromatograms of the reconstructed individual components; which are essentially the scaled chromatographic factors. The inset shows the negative lobes of the overlapped peaks. The bottom plot contains results of ten iterations of MCR with non-negativity applied in both domains and initialized using the varimax-rotated PCA factors. Peak labels correspond to peak numbers in Table 1. The amplitude of peak 9 has been increased by a factor of 10 to improve visibility.

The chromatographic factors for the varimax-rotated PCA analysis are presented in the top plot of FIG. 6. While it is difficult to see, the extent of negativity in the factors is very small, even in the presence of overlap in the second and third peaks with centers at 3.67 and 3.71 minutes. For ease of viewing, the scale of this region was expanded and superpositioned in the plot. Given the excellent performance of the rotated PCA algorithm, minimal refinement with MCR was required. The bottom plot of FIG. 6 contains the MCR factors of the nine-factor model initialized using the varimax solution and completing only 10 iterations. Again, the expansion of the overlap region demonstrates the ability of MCR with non-negativity constraints to "unmix" these factors. The MCR mass spectral factors for the nine components are displayed in FIG. 7.

Figure 7:
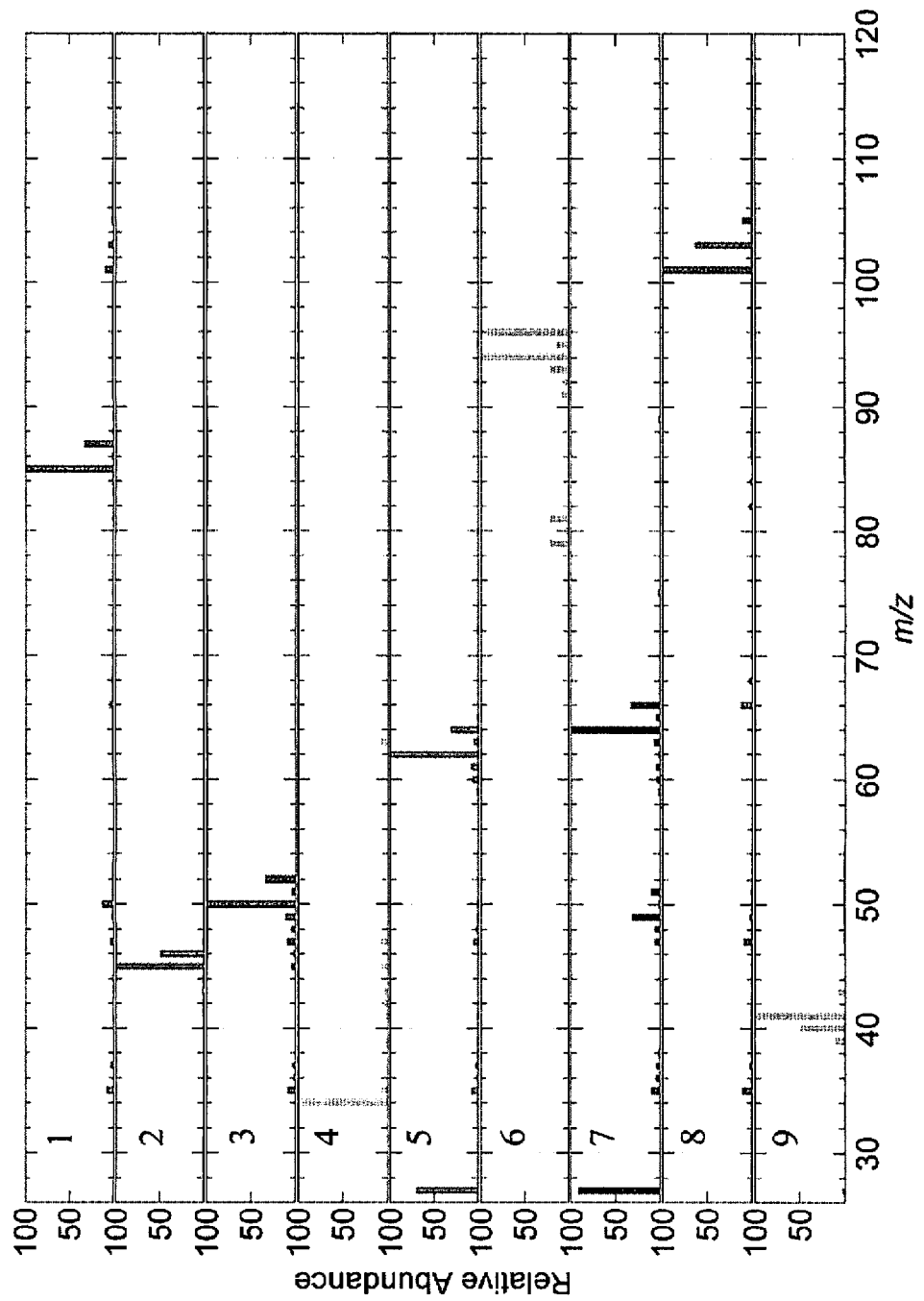
FIG. 7 shows the mass spectral factors for 10 iterations of MCR initialized with varimax-rotated, nine-factor PCA model. MCR employed non-negativity in both domains. Factors correspond to factors in the bottom plot of FIG. 6.

Identities of the six expected chemical species; with peak labels 1, 3, 5, 6, 7, and 8 in FIGS. 4, 6, and 7 and Table 1; were confirmed using the mass spectral factors as inputs to a NIST mass spectral library search routine. In addition, the NIST routine identified peak 2 as dimethyl ether, a common contaminant of methanol; and peak 9 as acetonitrile, with a confirmatory match factor of >860. The presence of acetonitrile was confirmed by comparing its elution time to that of an independent experiment involving only acetonitrile in methanol. The identity of the final species eluting as peak 4, was not revealed using the NIST mass spectral library search routine. This lack of library match is not unexpected because this factor is believed to represent ion-molecule reactions of methanol in the mass spectrometer source and thus not a separate distinct compound. The most abundant ion observed in the factors of peak 4 (see FIG. 7) was m/z 34. For methanol there is a small (0.21%) isotopic contribution at m/z 34, likely which also has abundance from protonated methanol. This factor demonstrates the sensitivity of the method to very low abundance chromatographic peaks.

TABLE 1

Chemical species assignments made from mass spectral factors derived from MCR analysis of VOC Mix 6 data.

| Peak | Elution Time (min) | Chemical Compound (NIST Library Assigned) |
|---|---|---|
| 1 | 3.52 | Dichlorodifluoromethane |
| 2 | 3.67 | Dimethyl ether† |
| 3 | 3.71 | Chloromethane |
| 4 | 3.83 | Unknown* |
| 5 | 3.89 | Vinyl chloride |
| 6 | 4.33 | Bromomethane |
| 7 | 4.50 | Ethyl chloride |
| 8 | 5.11 | Trichloromonofluoromethane |
| 9 | 5.31 | Acetonitrile** |

Notes:
†Dimethyl ether believed to be a contaminant from methanol solvent.
*Contaminant was unidentified.
**Acetonitrile contaminant was from an unknown source, but may be column or system carryover.

Factor Analysis of VOC Mix 8 Data

The original VOC Mix 8 data were collected over a time range of approximately 34 minutes constituting nearly 12,000 elements, and a mass range m/z: 27-371 comprising 240 nonzero mass channels. Initial data trimming reduced the time domain to 3-24 minutes (7554 elements) and the mass range m/z: 27-355 (148 mass channels), including SID of methanol m/z (28-33). The top plot in FIG. 8 contains expanded-scale total ion chromatogram of the raw data as well as the SID plot with the methanol m/z eliminated. As in VOC Mix 6, complete loss of the methanol peak and its long tail are dramatic. The twelve major peaks have been numbered for convenience, and their expected identities, as per NIST MS library matching, are contained in Table 2. The table lists only the "best hit", which misassigned the dichloroethylene, xylene, and dichlorobenzene isomers. This is common for these types of isomers in many other types of data processing; and under such circumstances GC/MS practitioners typically will employ retention time information or Kovats indices for confirmation. Browsing the NIST library matching results, the correct assignment in each case is within 1% of the "best hit" match score, and thus these misassignments are of minor concern. The important point is that the MCR is correctly modeling and separating the peaks. In addition to the eleven known constituents of the mix, the first peak is that of dimethoxymethane. FIG. 9 is a scree plot of the eigenvalues of the Poisson-scaled data after trimming the time domain and removal of the methanol m/z channels. Unfortunately, in this plot there is not a distinct or obvious transition from data eigenvalues to noise eigenvalues. Upon expansion of the plot, a 25-factor model was estimated to be appropriate.

TABLE 2

Chemical species assignments made from mass spectral factors derived from MCR analysis of VOC Mix * data.

| Peak | MCR Factor | Expected Chemical Compound | Elution Time (min) | Chemical Compound (NIST Library Assigned) |
|---|---|---|---|---|
| 1 | A | Dimethoxymethane | 5.80 | Dimethoxymethane |
| 2 | B | trans-1,2-Dichloroethylene | 7.13 | cis-1,2-Dichloroethylene |
| 3 | C | cis-1,2-Dichloroethylene | 8.33 | trans-1,2-Dichloroethylene |
| 4 | D | 1,2-Dichloropropane | 11.20 | 1,2-Dichloropropane |
| 5 | E | Toluene | 13.00 | Toluene |
| 6 | F | PCE | 14.01 | PCE |
| 6 | G | PCE | 14.03 | PCE |
| 7 | H | Chlorobenzene | 15.03 | Chlorobenzene |
| 8 | I | Ethylbenzene | 15.30 | Ethylbenzene |
| 9 | J | p-Xylene | 15.52 | m-Xylene |
| 10 | K | Styrene | 15.99 | Styrene |
| 11 | (I,J) | o-Xylene | 16.02 | |
| 12 | L | 1,2-Dichlorobenzene | 19.00 | 1,3-Dichlorobenzene |
| 12 | M | 1,2-Dichlorobenzene | 19.01 | 1,4-Dichlorobenzene |

Figure 8:
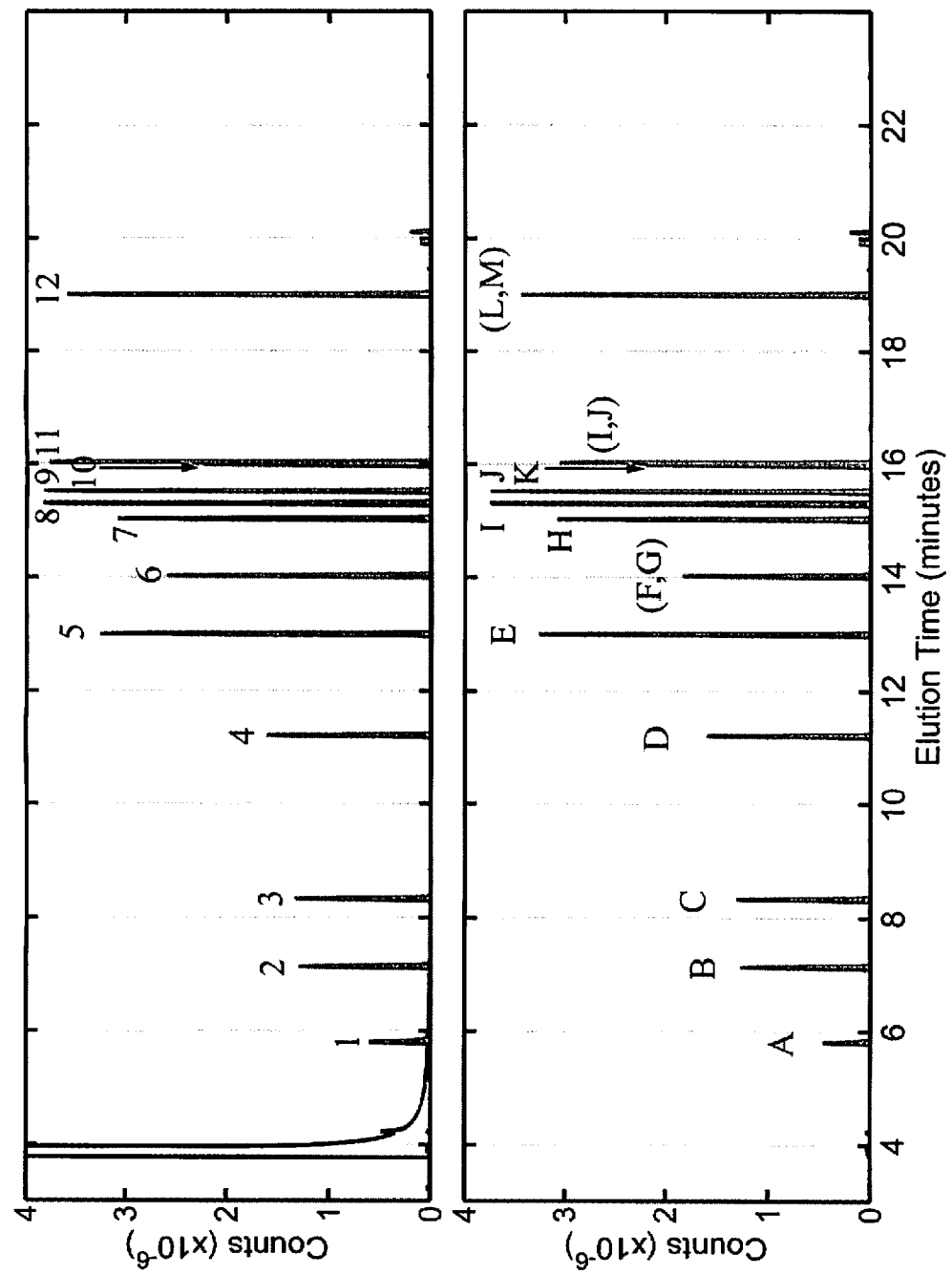
FIG. 8 shows ion chromatograms for volatile organic compound mixture VOC Mix 8. The top plot displays the comparison of the total ion chromatograms of the raw VOC Mix 8 GC/MS data and of the same data after SID removing m/z 28-33. The bottom plot contains results of ten iterations of MCR with non-negativity applied in both domains and initialized using the 25-factor model, varimax-rotated PCA-factors.
Figure 9:
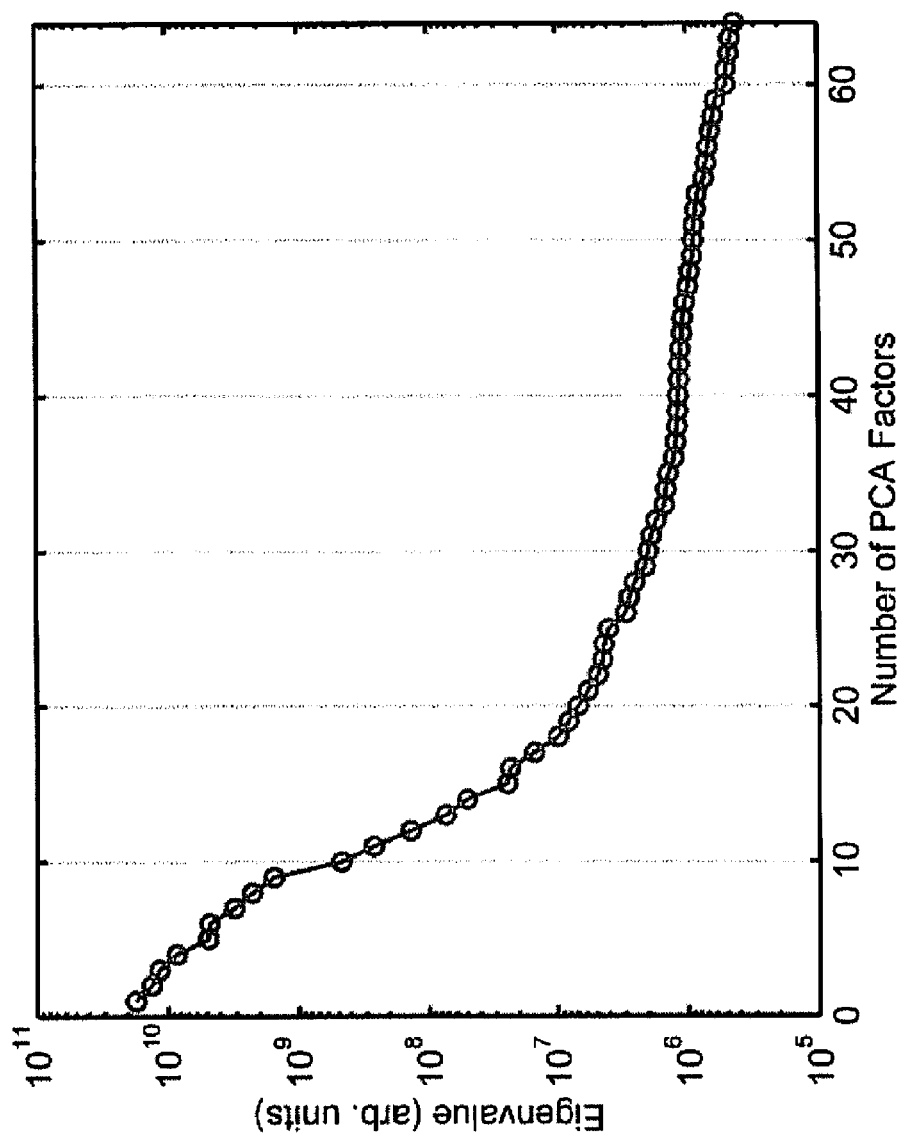
FIG. 9 is a graph of the eigenvalues of Poisson-scaled GC/MS VOC Mix 8 data plotted versus PCA factor number.
Figure 10:
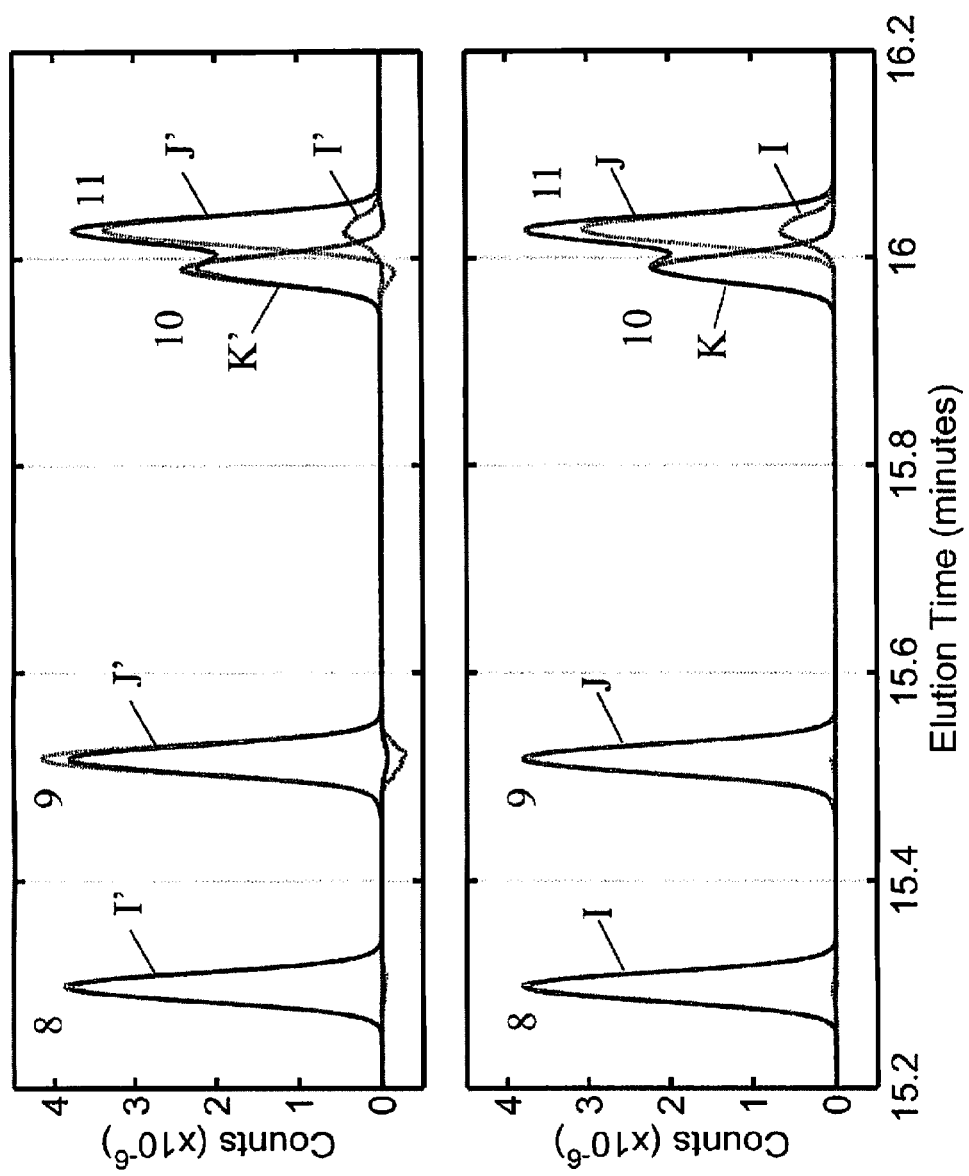
FIG. 10 shows the chromatographic factors for rotated and refined PCA solutions for the VOC Mix 8 data. The top plot contains the chromatographic factors from the varimax-rotated PCA of the Poisson-scaled SID data for VOC Mix 8 over the elution time period 15.2-16.2 minutes. The plot shows the total ion chromatogram of the SID data and scaled PCA chromatographic factors I', J', and K'. The bottom plot shows the chromatographic factors for 10 iterations of MCR initialized with varimax-rotated, 25-factor PCA model. MCR employed non-negativity in both domains. The peaks from left to right are ethylbenzene (8), p-xylene (9), styrene (10) and o-xylene (11). Ethylbenzene, p-xylene and styrene are modeled by MCR factors I, J and K, respectively; while o-xylene is modeled as contributions from both factors I and J.

The bottom plot in FIG. 8 contains the rank-25 model, chromatographic factors from MCR, initiated using the varimax-rotated PCA solution. All of the major peaks were modeled, plus a significant number of minor peaks. A lettering scheme for the thirteen major MCR factor peaks that model the twelve major data elution peaks was used. Species whose mass spectra are highly correlated pose a special problem; the results plotted in FIG. 10 represent one such challenge.

The species giving rise to the peaks displayed in FIG. 8 are, from left to right, ethylbenzene (8), p-xylene (9), styrene (10), and o-xylene (11). The first two peaks at times 15.3 and 15.5 minutes are well resolved, but have very similar, but discernable, mass spectra; so they are separable with PCA and MCR. The second two peaks are highly overlapped, but have very different mass spectra, so they are mostly separable with varimax-PCA with significant negative-going lobe so as to be orthogonal. The problem arises because the mass spectra of ethylbenzene, p-xylene, and o-xylene are so similar that the o-xylene peak is best modeled as a linear combination of ethylbenzene and p-xylene. A separate analysis of the data was conducted for all times greater than 15.8 minutes and a distinct peak for styrene at 15.99 minutes and another distinct peak for o-xylene at 16.02 minutes were obtained. While having to partition the data matrix in this manner not the most desirable situation, it does represent an option for identifying isomeric species whose mass spectra are nearly indistinguishable.

Figure 11:
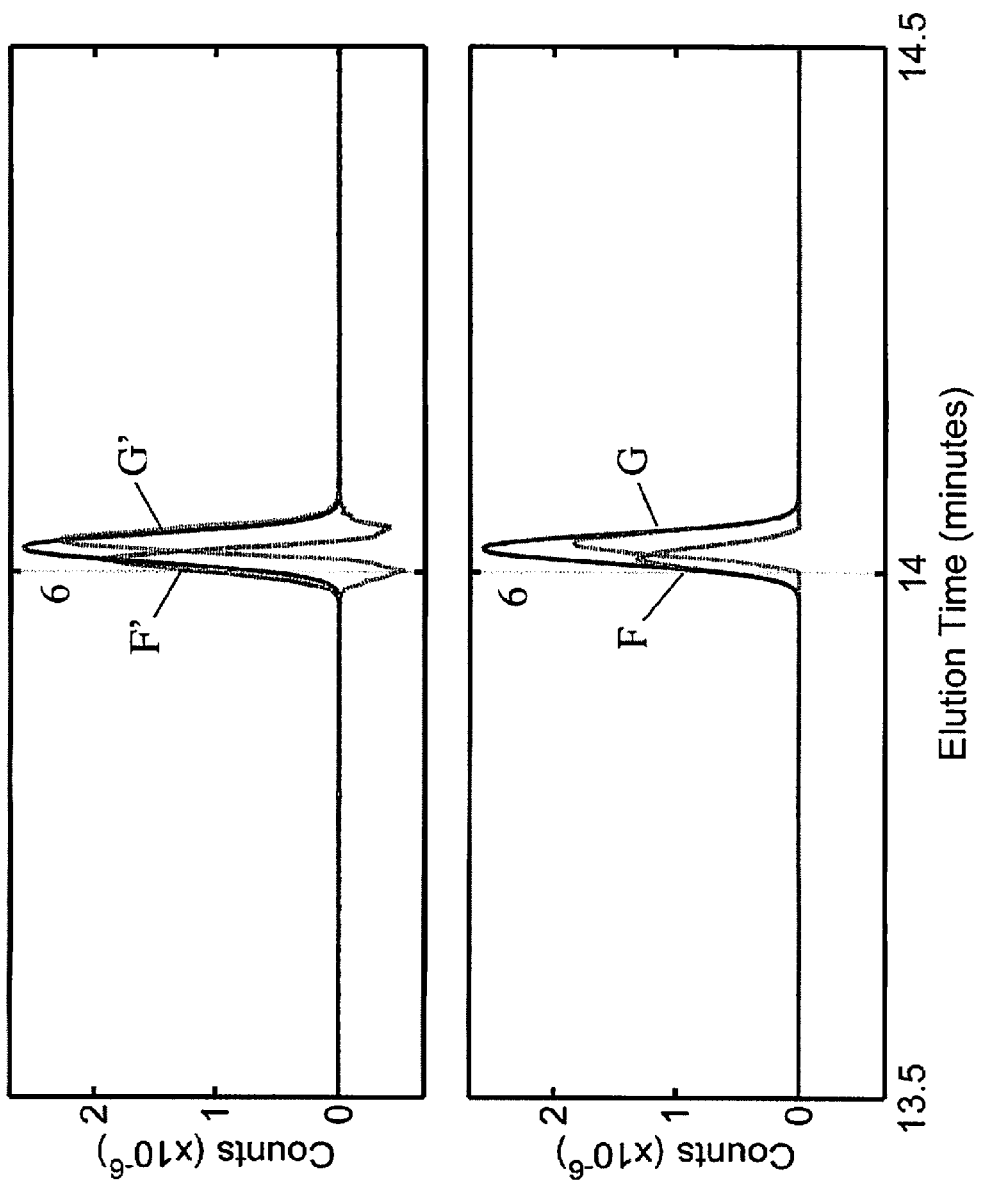
FIG. 11 shows the chromatographic factors for rotated and refined PCA solutions for the VOC Mix 8 data. The top plot contains peak 6, PCE, and the chromatographic factors from the varimax-rotated PCA of the Poisson-scaled SID data for VOC Mix 8. The plot shows the total ion chromatogram of the SID data and scaled PCA chromatographic factors F' and G'. The bottom plot is the chromatographic factors for 10 iterations of MCR initialized with varimax-rotated, 25-factor PCA model. MCR employed non-negativity in both domains. Factor F is the lighter chlorine isotope PCE and G is the heavier isotope.
Figure 12:
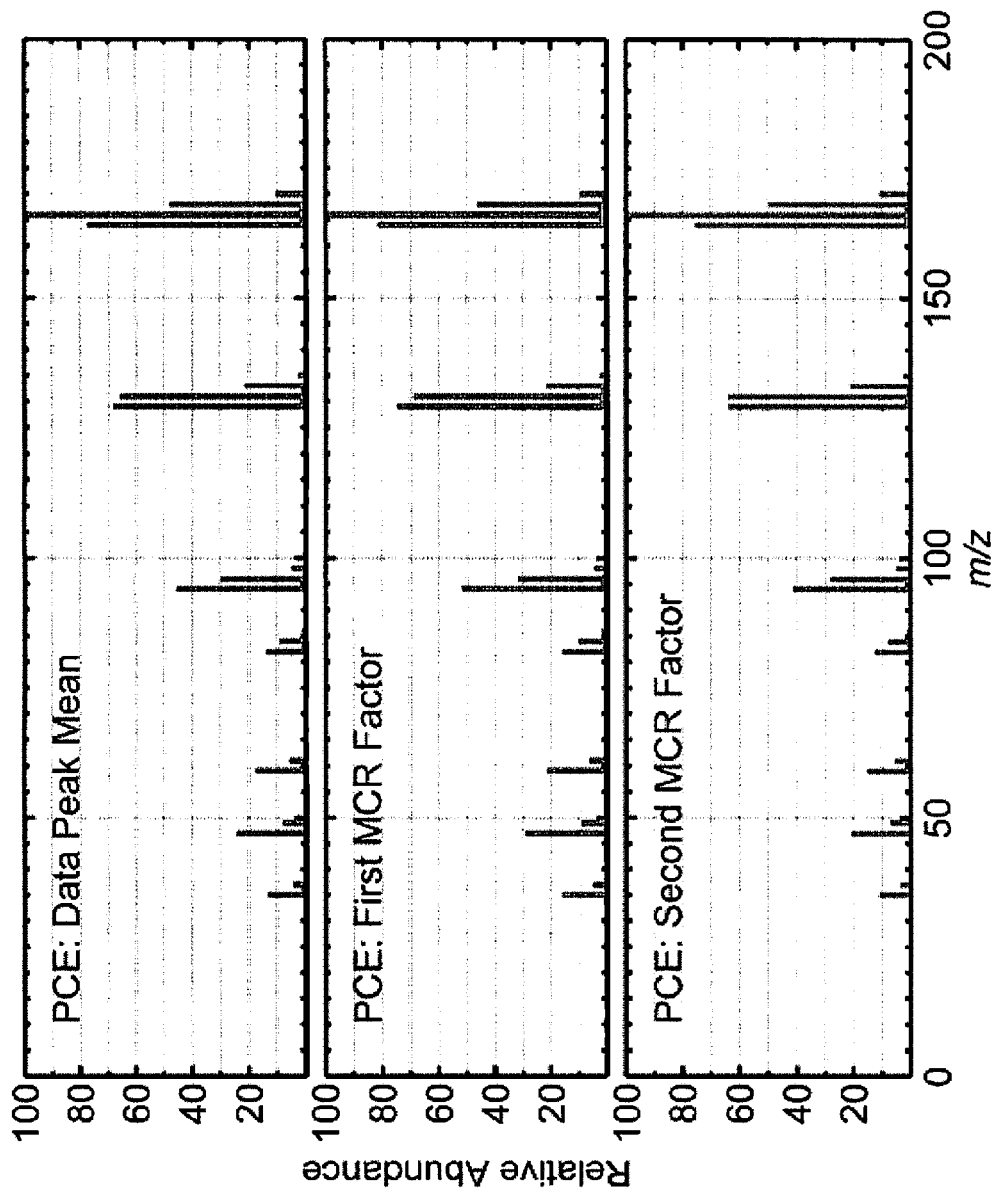
FIG. 12 shows the mass spectra of average PCE peak (6) and as estimated from MCR. The top plot shows the mean mass spectrum of SID data for the elution times 13.5-14.5 minutes. The middle plot shows the mass spectral MCR factor for the early eluting PCE factor. The bottom plot shows the mass spectral MCR factor for the later eluting PCE factor.

Perhaps the most impressive demonstration of the power of the method of the present invention is represented in FIG. 11. The top plot shows the elution peak for PCE 6 its two varimax-rotated PCA factors in F' and G'. Due to orthogonality constraints the peaks have both positive and negative lobes. Even in the bottom plot, the MCR results nicely resolve the two peaks F and G with Gaussian shapes. FIG. 12 contains the peak-integrated mass spectrum, and the mass spectral factors of the first factor (left) and second factor (right) in the top, middle, and bottom panels, respectively. These plots reveal chlorine isotope abundance dependence as a function of elution time. An analysis of these plots is found in Tables 3-5. The theoretical probability for the two, three and four chlorine fragments using a binomial probability distribution and a 24.22% natural abundance for $^{37}Cl$. See D. R. Lide, Ed. *CRC Handbook of Chemistry and Physics*, 84 ed.; CRC Press: Boca Raton, Fla. (2003).

Table 3 is a comparison of the theoretical and actual proportions of $C_2Cl_2$ fragment for the possible combinations of $^{35}Cl$ and $^{37}Cl$. A comparison of the theoretical proportions with that of the integrated peak of the raw data shows excellent agreement, as well as with the NIST Standard Data. However, the first (left) peak appears to have enrichment in the lighter isotope since its 0/2 $^{37}Cl/^{35}Cl$ proportion is larger than the expected value while the 2/0 $^{37}Cl/^{35}Cl$ proportion is lower than expected. In contrast, the second (right) peak values show enrichment in the heavier isotope. This pattern is repeated in the subsequent tables: enrichment of $^{35}Cl$ in the left peak and complementary enrichment of $^{37}Cl$ in the right peak. This is entirely consistent with isotopic behavior in a diffusion controlled process.

TABLE 3

Probabilities and actual proportions calculated for the two-chlorine fragments of PCE.

| $^{37}Cl/^{35}Cl$ ratio: | 0/2 | 1/1 | 2/0 |
|---|---|---|---|
| Mass $C_2Cl_2$ | 94 | 96 | 98 |
| Theoretical Prob. (%): | 57.4 | 36.7 | 5.9 |
| Raw Data Dist. (%): | 56.9 | 37.1 | 6.0 |
| Peak One Dist. (%): | 58.8 | 36.1 | 5.1 |
| Peak Two Dist. (%): | 55.8 | 37.8 | 6.4 |
| NIST data Dist. (%): | 56.7 | 37.2 | 6.1 |

TABLE 4

Probabilities and actual proportions calculated for the three-chlorine fragments of PCE.

| $^{37}Cl/^{35}Cl$ ratio: | 0/3 | 1/2 | 2/1 | 3/0 |
|---|---|---|---|---|
| Mass $C_2Cl_3$ | 129 | 131 | 133 | 135 |
| Theoretical Prob. (%): | 43.5 | 41.7 | 13.3 | 1.4 |
| Raw Data Dist. (%): | 43.2 | 41.7 | 13.5 | 1.5 |
| Peak One Dist. (%): | 44.6 | 41.2 | 12.8 | 1.3 |
| Peak Two Dist. (%): | 42.3 | 42.2 | 13.9 | 1.5 |
| NIST data Dist. (%): | 42.6 | 42.4 | 13.6 | 1.4 |

TABLE 5

Probabilities and actual proportions calculated for cationic PCE.

| $^{37}Cl/^{35}Cl$ ratio: | 0/4 | 1/3 | 2/2 | 3/1 | 4/0 |
|---|---|---|---|---|---|
| Mass $C_2Cl_4$ | 166 | 168 | 170 | 170 | 172 |
| Theoretical Prob. (%): | 33.0 | 42.2 | 20.2 | 4.3 | 0.3 |
| Raw Data Dist. (%): | 32.8 | 42.2 | 20.3 | 4.3 | 0.3 |
| Peak One Dist. (%): | 34.3 | 42.0 | 19.4 | 4.0 | 0.3 |
| Peak Two Dist. (%): | 32.0 | 42.3 | 20.9 | 4.5 | 0.4 |
| NIST Data Dist. (%): | 33.3 | 41.2 | 20.7 | 4.5 | 0.3 |

The present invention has been described as method for factor analysis of GC/MS data. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for factor analysis of GC/MS data, comprising:
    a) measuring a mass-charge (m/z) spectrum of a sample with a gas chromatograph/mass spectrometer (GC/MS), whereby the spectrum is represented an m×n matrix of GC/MS data D, wherein m is a number of mass spectra and n is a number of eluted chromatographic peaks;
b) factoring the data matrix D into the product of an m×p matrix of orthogonal scores vectors T and an n×p matrix of orthonormal loading vectors P using Principal Component Analysis (PCA) to provide a PCA solution $D=TP^T$, wherein p is a pseudorank;
c) rotating the loading matrix P, according to $\underline{P}=PR$, to provide a rotated loading matrix $\underline{P}$ of chromatographic factors, wherein R is an orthogonal rotation matrix; and
d) rotating the scores matrix T, according to $\underline{T}=TR$, to provide a rotated scores matrix $\underline{T}$ of mass spectral factors and a rotated data matrix, according to $D=\underline{T}\underline{P}^T$.

2. The method of claim 1, further comprising the step of selective ion depletion of peaks in the m/z spectrum for one or more dominant species in the sample prior to step a).

3. The method of claim 1, wherein step b) comprises non-linear iterative partial least squares, eigenanalysis, or singular value decomposition.

4. The method of claim 1, wherein the pseudorank p in step b) represents a number of chemically meaningful species in the sample.

5. The method of claim 1, wherein the rotation matrix R in step b) is determined using a varimax procedure.

6. The method of claim 1, further comprising scaling the data matrix D prior to step b) and rescaling the rotated data matrix after step d).

7. The method of claim 6, wherein the data matrix D is scaled according to $\hat{D}=HD$ where the diagonal matrix H is a diagonal matrix whose diagonal elements are $\bar{d}_m^{-1/2}$ and wherein the m×n data matrix D is oriented as mass spectral domain by chromatographic domain with mean m/z spectrum $\bar{d}_m$ given by $$\bar{d}_m = \frac{1}{n}D1_n.$$

8. The method of claim 1, further comprising refining the PCA solution, according to $D=\underline{T}\underline{P}^T=MC^T$, to provide an m×p matrix M of refined mass spectral factors and an n×p matrix C of refined chromatographic factors.

9. The method of claim 8, wherein the refining comprises refining the rotated loading matrix $\underline{P}$.

10. The method of claim 9, wherein the refining comprises constrained least-squares, according to $$\underline{P} \leftarrow \min_{\underline{P}|\underline{T}}\|D - \underline{P}\,\underline{T}^T\|_F.$$

11. The method of claim 9, further comprising refining the rotated scores matrix $\underline{T}$.

12. The method of claim 11, wherein the refining comprises constrained alternating least squares, wherein given a refined $\underline{P}$, a refined $\underline{T}$ is computed, subject to constraints, according to $$\underline{T} \leftarrow \min_{\underline{T}|\underline{P}}\|D - \underline{P}\,\underline{T}^T\|_F.$$

13. The method of claim 12, wherein the refining comprises non-negative matrix factorization.

* * * * *